(12) United States Patent
Chapman et al.

(10) Patent No.: US 10,628,767 B2
(45) Date of Patent: Apr. 21, 2020

(54) ENCOUNTER MANAGEMENT

(71) Applicant: Invidasys, Inc., Mesa, AZ (US)

(72) Inventors: Sherwood Chapman, Gilbert, AZ (US); Rasesh Joshi, Denver, CO (US); Karen Bunkley, Gilbert, AZ (US)

(73) Assignee: INVIDASYS, INC., Mesa, AZ (US)

( * ) Notice: Subject to any disclaimer, the term of this patent is extended or adjusted under 35 U.S.C. 154(b) by 834 days.

(21) Appl. No.: 15/198,445

(22) Filed: Jun. 30, 2016

(65) Prior Publication Data

US 2017/0004265 A1    Jan. 5, 2017

Related U.S. Application Data

(60) Provisional application No. 62/186,652, filed on Jun. 30, 2015.

(51) Int. Cl.
| | |
|---|---|
| *G06Q 10/06* | (2012.01) |
| *G06F 16/23* | (2019.01) |
| *G06F 16/84* | (2019.01) |
| *G06F 19/00* | (2018.01) |
| *G06Q 50/22* | (2018.01) |

(52) U.S. Cl.
CPC ..... *G06Q 10/0633* (2013.01); *G06F 16/2358* (2019.01); *G06F 16/86* (2019.01); *G06F 19/328* (2013.01); *G06Q 50/22* (2013.01)

(58) Field of Classification Search
CPC .... G06Q 10/0633; G06Q 50/22; G06F 16/86; G06F 16/2358; G06F 19/328
See application file for complete search history.

(56) References Cited

U.S. PATENT DOCUMENTS

| | | |
|---|---|---|
| 7,225,411 B1 | 5/2007 | Stoner et al. |
| 7,509,655 B2 | 3/2009 | Willis et al. |
| 7,739,132 B2 | 6/2010 | Denny, Jr. et al. |
| (Continued) | | |

OTHER PUBLICATIONS

Oracle Workflow Enables E-Business Integration, http://www.oracle.com/technetwork/testcontent/workflow-fov-083284.html?printOnly=1, accessed Jun. 4, 2014.

*Primary Examiner* — Eliza A Lam
(74) *Attorney, Agent, or Firm* — Bryan Cave Leighton Paisner LLP

(57) ABSTRACT

A method including: receiving one or more encounters to be submitted to one or more governmental entities for reimbursement after the encounters have been adjudicated and paid by a health insurance plan; verifying whether each of the one or more encounters comply with regulations specified by the one or more governmental entities to determine one or more improper encounters of the one or more encounters comprising one or more errors that do not comply with the regulations specified by the one or more governmental entities; correcting the one or more improper encounters of the one or more encounters to comply with the regulations specified by the one or more governmental entities; submitting the one or more encounters, including the one or more improper encounters, as corrected, to the one or more governmental entities for reimbursement; and receiving one or more responses from the one or more governmental entities corresponding to the one or more encounters. Other embodiments are provided.

20 Claims, 26 Drawing Sheets

(56) References Cited

U.S. PATENT DOCUMENTS

| | | | |
|---|---|---|---|
| 7,752,096 B2 * | 7/2010 | Santalo | G06Q 20/102 |
| | | | 705/2 |
| 7,788,115 B2 | 8/2010 | Flam et al. | |
| 7,797,172 B2 * | 9/2010 | Fitzgerald | G06F 19/328 |
| | | | 705/4 |
| 8,108,274 B2 | 1/2012 | Johnston et al. | |
| 8,139,742 B2 | 3/2012 | Klos et al. | |
| 8,447,627 B1 | 5/2013 | Cruise | |
| 8,645,168 B2 | 2/2014 | Schmidt et al. | |
| 8,655,685 B2 | 2/2014 | Denny, Jr. et al. | |
| 8,719,057 B2 | 5/2014 | Denny, Jr. et al. | |
| 9,020,826 B2 | 4/2015 | Marvin et al. | |
| 9,916,369 B2 | 3/2018 | Pearson et al. | |
| 2004/0133452 A1 * | 7/2004 | Denny, Jr. | G06F 19/328 |
| | | | 705/2 |
| 2005/0288972 A1 | 12/2005 | Marvin et al. | |
| 2007/0073685 A1 | 3/2007 | Thibodeau et al. | |
| 2008/0040702 A1 | 2/2008 | Sciacero et al. | |
| 2008/0147436 A1 * | 6/2008 | Ohlsson | G06Q 10/087 |
| | | | 705/2 |
| 2009/0326974 A1 | 12/2009 | Tolan et al. | |
| 2010/0318393 A1 | 12/2010 | Acker et al. | |
| 2011/0029321 A1 | 2/2011 | Rourke et al. | |
| 2011/0258004 A1 | 10/2011 | Dean et al. | |
| 2013/0158964 A1 | 6/2013 | Hall et al. | |
| 2014/0046678 A1 | 2/2014 | Lacy et al. | |

\* cited by examiner

Data Filter

Filter Name      Billing - PRV Add  ← 511
Update Filter    True  ← 512
Updated          2/17/2015 3:45:04 PM
Updated By       Daryl

Details

Show [10 ▼] entries                                                                 Search: [          ]

| Xml Data | Segment | Element | Conditional | Value |  |  |
|---|---|---|---|---|---|---|
| ◇ | ◇ | ◇ | ◇ | ◇ Conditional Value | | Add |
| ▶ | Search for a Segment Name | ▽ | ▽ | | | |
| True | PRV_BillingProviderSpecialtyInformation | PRV02_ReferenceIdentificationQualifier | Update | PXC | | Delete |
| True | PRV_BillingProviderSpecialtyInformation | PRV03_ProviderTaxonomyCode | Create | | | Delete |
| True | PRV_BillingProviderSpecialtyInformation | PRV01_ProviderCode | Create | BI | ⬆⬇ | |

Showing 1 to 4 of 4 entries

513

500

Details  Index

Data Filter

| | |
|---|---|
| Filter Name | Principal Diag POA Indicator — 511 |
| Update Filter | False — 512 |
| Updated | 2/12/2015 4:49:38 PM |
| Updated By | karen |

513

Details

Show [10 ▽] entries          Search: [      ]

| XmlData ◇ | Segment ◇ | Element ◇ | Conditional ◇ | Value ◇ | |
|---|---|---|---|---|---|
| | Search for a Segment Name | | equals ▽ | Conditional Value | Add |
| True | C023_HealthCareServiceLocationInformation | C02301_FacilityTypeCode | equals | 11 | Delete |
| True | C023_HealthcareCodeInformation | C02202_PrincipalDiagnosisCode | not equal to | | Delete |
| True | C022_HealthCareCodeInformation | C02209_PresentAdmissionIndicator | less than | | |
| | | | greater than | | |
| | | | begins with | | |
| | | | ends with | | |
| | | | contains | | |
| | | | does not contain | | |
| | | | exists | | |
| | | | missing | | |
| | | | length equals | | |
| | | | length greater than | | |
| | | | length less than | | |

Showing 1 to 4 of 4 entries

Details  Index

XmlDictionarySchema

← 910

Show [250 ▽] entries     Search: [        ]

| Name ◇ | Created ◇ | Created By ◇ | Updated ◇ | Updated By ◇ | ◇ |
|---|---|---|---|---|---|
| Meds III - Dental | 11/20/2014 12:00:00 AM | ed | 11/20/2014 12:00:00 AM | ed | Delete |
| Meds III - Institutional | 11/20/2014 2:28:19 PM | ed | 11/20/2014 2:28:19 PM | ed | Delete |
| Meds III - Pharmacy | 11/20/2014 12:00:00 AM | ed | 11/20/2014 12:00:00 AM | ed | Delete |
| Meds III - Professional | 11/20/2014 12:00:00 AM | ed | 11/20/2014 12:00:00 AM | ed | Delete |
| NCPDP 2.2 | 12/18/2014 12:15:56 PM | ed | 12/18/2014 12:15:56 PM | ed | Delete |
| RAPS | 2/10/2015 11:35:00 AM | ed | 2/10/2015 11:35:00 AM | ed | Delete |
| X12_00501_276 | 3/31/2014 6:54:52 AM | ED | 3/31/2014 6:54:52 AM | ED | Delete |
| X12_00501_277 | 3/31/2014 6:54:58 AM | ED | 3/31/2014 6:54:58 AM | ED | Delete |
| X12_00501_834 | 3/30/2014 2:47:54 PM | ed | 3/30/2014 2:47:54 PM | ed | Delete |
| X12_00501_835 | 3/30/2014 2:47:41 PM | ed | 3/30/2014 2:47:41 PM | ed | Delete |
| X12_00501_837_D | 11/4/2014 11:17:35 AM | ed | 11/4/2014 11:17:35 AM | ed | Delete |
| X12_00501_837_I | 3/27/2014 7:19:10 AM | ed | 3/27/2014 7:19:10 AM | ed | Delete |
| X12_00501_837_P | 3/27/2014 7:18:57 AM | ed | 3/27/2014 7:18:57 AM | ed | Delete |

Showing 1 to 13 of 13 entries

FIG. 9

▷ Dental Encounters
▽ Institutional Encounters

| Queues | Trends | Aging | 837I-REMOVEDPRV-721test file-(7).text |
|---|---|---|---|
| Adjustment/Void | Today | Day Range 1 - 11 | KYW837I_9900000695_O_20130214_060527_P.txt |
| Bad Dates | Tuesday | Day Range 12 - 22 | |
| Billing - Tax Identification | Monday | Day Range 23 - 33 | |
| Charges out of balance | Sunday | Day Range 34 - 44 | |
| Claim Issues | Saturday | Day Range 45 - 55 | |
| Duplicate Encounters | Friday | Day Range 56 - 66 | |
| E-Code | Thursday | Day Range 67 - 77 | |
| Interim Bill | Wednesday | Day Range 78 - 88 | |
| Invalid Field length | | Day Range 89 - 99 | |
| Invalid HIC Number | | Day Range 100 - 110 | |
| Invalid Segment/Loop | | Day Range 111 - 121 | |
| Missing Rendering | | Day Range 122 - 132 | |
| Missing Segment | | Day Range 133 - 143 | |
| N402/N403 Missing | | Day Range 144 - 154 | |
| Name Issues | | Day Range 155 - 165 | |
| NPI Issues | | | |
| PO Box Not Allowed | | | |
| Provider Taxonomy | | | |
| Repricing Issues | | | |
| Subscriber Issues | | | |
| Zip Code Issues | | | |

Queue Action

Show [10 ▽] entries        Search: [   ] ← 1110

| Encounter ID ◁ ◇ | Status ◇ | Created ◇ | Created By ◇ | Updated ◇ | Updated By ◇ | | |
|---|---|---|---|---|---|---|---|
| 14268AA013 | ADJHOLD | 9/25/2014 3:47:38 PM | BiztalkHost | 12/5/2014 4:18:37 PM | dbo | Details | Edit |
| 14268AA015 | ADJHOLD | 9/25/2014 3:50:03 PM | BiztalkHost | 12/5/2014 4:18:37 PM | dbo | Details | Edit |
| 14268AA019 | ADJHOLD | 9/25/2014 3:52:25 PM | BiztalkHost | 12/5/2014 4:18:37 PM | dbo | Details | Edit |
| 14268AA020 | ADJHOLD | 9/25/2014 4:03:41 PM | BiztalkHost | 12/5/2014 4:18:37 PM | dbo | Details | Edit |
| 14280AA030 | REVIEW | 10/7/2014 9:55:56 AM | BiztalkHost | 12/29/2014 12:53:05 PM | dbo | Details | Edit |
| 14280AA030 | REVIEW | 10/7/2014 9:55:56 AM | BiztalkHost | 12/29/2014 12:53:05 PM | dbo | Details | Edit |
| 14280AA030 | REVIEW | 10/7/2014 10:06:20 AM | Control | 12/29/2014 12:54:08 PM | dbo | Details | Edit |
| 14280AA074 | REVIEW | 10/7/2014 10:06:20 AM | Control | 12/29/2014 12:54:08 PM | dbo | Details | Edit |
| 14280AA074 | REVIEW | 10/7/2014 10:06:20 AM | Control | 12/29/2014 12:54:08 PM | dbo | Details | Edit |

Showing 1 to 10 of 100 entries

FIG. 11

Queue for transaction(86a55fb6-6bc8-4ed9-8dd3-b1a56d123f6b)

Transaction

| Component | Transaction Name |
|---|---|
| VIDACounter | Institutional Encounters |

Details — 1210

Create new

Show [250 ▽] entries                                Search: [      ]

| Transaction Sequence No | Queue Name | Owner Role | Is Active | Days To Release | Threshold | Created | Created by | Updated | Updated By | | |
|---|---|---|---|---|---|---|---|---|---|---|---|
| ◁ ◇ | ◇ | ◇ | ◇ | ◇ | ◇ | ◇ | ◇ | ◇ | ◇ | ◇ | |
| Institutional Encounters | Provider Taxonomy | Owner | True | | 100 | 3/31/2014 2:24:17 PM | ed | 5/12/2014 7:02:20 AM | Daryl | Edit | Delete |
| Institutional Encounters | Subscriber Issues | Is Users | True | | 102 | 4/5/2014 2:45:27 PM | Daryl | 10/14/2014 9:07:31 AM | Daryl | Edit | Delete |
| Institutional Encounters | Missing Rendering | Owner | True | | 101 | 3/31/2014 2:24:17 PM | ed | 10/14/2014 9:05:35 AM | Daryl | Edit | Delete |
| Institutional Encounters | Interim Bill | Is Users | True | | 20 | 7/8/2014 10:42:50 AM | terri | 10/14/2014 9:57:04 AM | Daryl | Edit | Delete |
| Institutional Encounters | Claim Issues | Is Users | True | | 20 | 4/5/2014 2:54:08 PM | Daryl | 4/5/2014 2:54:08 PM | Daryl | Edit | Delete |
| Institutional Encounters | Invalid HIC Number | Owner | True | | 100 | 3/31/2014 2:24:17 PM | ed | 3/31/2014 2:24:17 PM | ed | Edit | Delete |
| Institutional Encounters | Billing - Tax Identification | Is Users | True | | 100 | 3/31/2014 3:34:25 PM | Daryl | 3/31/2014 3:34:25 PM | Daryl | Edit | Delete |
| Institutional Encounters | Zip Code Issues | Owner | True | | 100 | 3/31/2014 2:24:17 PM | ed | 3/31/2014 2:24:17 PM | ed | Edit | Delete |
| Institutional Encounters | Name Issues | Owner | True | | 1000 | 3/31/2014 2:24:17 PM | ed | 3/31/2014 2:24:17 PM | ed | Edit | Delete |
| Institutional Encounters | PO Box Not Allowed | Owner | True | | 1000 | 3/31/2014 2:24:17 PM | ed | 3/31/2014 2:24:17 PM | ed | Edit | Delete |
| Institutional Encounters | Bad Dates | Owner | True | | 100 | 3/31/2014 2:24:17 PM | ed | 3/31/2014 2:24:17 PM | ed | Edit | Delete |
| Institutional Encounters | Invalid Segment/Loop | Owner | True | | 100 | 3/31/2014 2:24:17 PM | ed | 3/31/2014 2:24:17 PM | ed | Edit | Delete |
| Institutional Encounters | Charges out of balance | Owner | True | | 100 | 3/31/2014 2:24:17 PM | ed | 3/31/2014 2:24:17 PM | ed | Edit | Delete |
| Institutional Encounters | E-code | Owner | True | | 100 | 3/31/2014 2:24:17 PM | ed | 3/31/2014 2:24:17 PM | ed | Edit | Delete |
| Institutional Encounters | Invalid Field Length | Owner | True | | 100 | 3/31/2014 2:24:17 PM | ed | 3/31/2014 2:24:17 PM | ed | Edit | Delete |
| Institutional Encounters | Missing Segment | Owner | True | | 100 | 3/31/2014 2:24:17 PM | ed | 3/31/2014 2:24:17 PM | ed | Edit | Delete |

QueueUserDefinition

Create new

Show [10 ▼] entries          Search: [____]

| Role Description ◇ | Queue Username ◇ | Start Date ◇ | End Date ◇ | Created ◇ | Created By ◇ | Updated ◇ | Updated By ◇ | | | |
|---|---|---|---|---|---|---|---|---|---|---|
| Is Users | Jean R | 7/28/2014 11:28:11 AM | 12/31/2078 11:28:11 AM | 7/28/2014 11:28:29 AM | terri | 7/28/2014 11:28:29 AM | terri | Details | Edit | Delete |
| Is Users | Belinda | 12/9/2014 4:37:58 PM | 12/9/2015 4:37:58 PM | 12/9/2014 4:38:07 PM | Belinda | 12/9/2014 4:38:07 PM | Belinda | Details | Edit | Delete |
| Is Users | karen | 10/29/2014 9:09:16 AM | 12/31/2020 12:00:00 AM | 10/29/2014 9:09:39 AM | karen | 10/29/2014 9:09:39 AM | karen | Details | Edit | Delete |
| Is Users | Daryl | 1/1/2014 12:00:00 AM | 12/20/2078 12:00:00 AM | 5/1/2014 12:35:16 PM | Daryl | 6/25/2014 4:34:10 PM | Daryl | Details | Edit | Delete |
| Is Users | Ankur | 8/25/2014 2:17:42 PM | 8/25/2015 2:17:42 PM | 8/25/2014 2:17:48 PM | Ankur | 8/25/2014 2:17:48 PM | Ankur | Details | Edit | Delete |
| Is Users | Michele | 11/12/2010 12:00:00 AM | 12/31/2078 12:00:00 AM | 11/12/2014 3:38:41 AM | Michele | 11/12/2014 3:39:10 AM | Michele | Details | Edit | Delete |
| Owner | terri | 12/15/2014 10:19:40 AM | 12/15/2015 10:19:40 AM | 12/15/2014 10:19:47 AM | Belinda | 12/15/2014 10:19:47 AM | Belinda | Details | Edit | Delete |
| Owner | Belinda | 12/15/2014 10:15:38 AM | 12/15/2015 10:15:38 AM | 12/15/2014 10:15:48 AM | Belinda | 12/15/2014 10:15:48 AM | Belinda | Details | Edit | Delete |
| VIDACounter Issues | Daryl | 1/1/2014 12:00:00 AM | 12/31/2078 12:00:00 AM | 6/25/2014 4:20:54 AM | Daryl | 6/25/2014 4:20:54 PM | Daryl | Details | Edit | Delete |
| VIDAServ Queues | JimFallon | 11/11/2014 12:13:58 PM | 11/11/2015 12:13:58 PM | 11/11/2014 12:14:02 PM | Michael | 11/11/2014 12:14:02 PM | Michael | Details | Edit | Delete |

Showing 1 to 10 of 15 entries

1400 Transaction > Edit

* 837 Encounter P

Encounter Id — 14254AA006 ← 1411

Status — Review Encounter ▼ ← 1412

- BillingProviderHierarchicalLevelLoop
  - BillingProviderSpecialtyInformation
    - ProviderCode [BI]
    - ReferenceIdentificationQualifier
    - [PXC]
    - ProviderTaxonomyCode
    - [291U00000X]
  - BillingProviderName Loop
    - BillingProviderName
    - BillingProviderAddress
      - BillingProviderAddressLine [4531 W HARRISON ST]
    - BillingProviderCityStateZipCode
    - BillingProviderTaxIdentification
    - BillingProviderContactInformation
- SubscriberHierarchicalLevelLoop
- ClaimInformationLoop
- ServiceLineNumber 1
- ServiceLineNumber 2
- ServiceLineNumber 3

← 1413

Show [10 ▼] entries     Search: [ ]

| Review Code | Description | Review Type Desc | Created | |
|---|---|---|---|---|
| [Search for a Review Code] | | | | Add |
| 2010AANM103 | Billing Provider Validation | Review | 2/10/2015 2:31:57 PM | Details |
| 2010BA103 | Member Validation | Review | 2/10/2015 2:31:57 PM | Details |
| 2300CLMDUP | Duplicate Encounter | Review | 2/10/2015 2:32:02 PM | Details |

Showing 1 to 4 of 4 entries

Status Codes
Create

Show [250 ▽] entries                                      Search: [          ]

| Status Code | Is Active | Description | | | |
|---|---|---|---|---|---|
| F96 | True | X-Ray Procedure Reduced To HFS Allowable | Details | Edit | Delete |
| X10 | True | X-Ray Procedure Previously Paid | Details | Edit | Delete |
| X64 | True | Web App Proofs/Sign Sent After Submit Day | Details | Edit | Delete |
| A41 | True | Void/Rebill is Past Timely Filing | Details | Edit | Delete |
| A97 | True | Void/Rebill Hold | Details | Edit | Delete |
| X15 | True | Visit Previously Paid | Details | Edit | Delete |
| I07 | True | Veterans Payment Reduced Copay/Coinsurance* | Details | Edit | Delete |
| E72 | True | Valid Unit Required for Epogen | Details | Edit | Delete |
| C47 | True | Valid Accident/Injury Code Required for Emergency Services | Details | Edit | Delete |
| D25 | True | Undefined Error -- Contact Department | Details | Edit | Delete |
| R48 | True | Type Of Care Requires Authorization | Details | Edit | Delete |
| U64 | True | Type Of Bill Invalid For Provider Type | Details | Edit | Delete |
| A00 | False | TST | Details | Edit | Delete |
| A52 | True | Transportation Modifier Invalid for Service | Details | Edit | Delete |
| T35 | True | TPL Status Invalid | Details | Edit | Delete |
| T05 | True | TPL Status Indicates TPL Amount Required | Details | Edit | Delete |
| T46 | True | TPL Invalid On Illinois Medicaid Line | Details | Edit | Delete |
| T38 | True | TPL Edit Bypass Preventative Services | Details | Edit | Delete |
| T37 | True | TPL Edit Bypass Pregnancy Related | Details | Edit | Delete |
| T03 | True | TPL Amount Indicates Status Is Incorrect | Details | Edit | Delete |
| F18 | True | TPL Amount Greater Than Department Maximum | Details | Edit | Delete |
| T10 | True | TPL Adjudication Date Illogical | Details | Edit | Delete |
| F26 | True | Total Deductions Recomputed | Details | Edit | Delete |
| F20 | True | Total Charges Recomputed | Details | Edit | Delete |
| C35 | True | TOS=Surgeon/Modifier= Surgical Assistant | Details | Edit | Delete |
| F17 | True | Third Party Source Not Identified | Details | Edit | Delete |
| T32 | True | Third Party Source Not Identified | Details | Edit | Delete |
| T07 | True | Third Party Date Implies Illogical Status | Details | Edit | Delete |
| T98 | True | Telepsychiatry Provider Invalid | Details | Edit | Delete |

Transaction
- 21 - 345
- A46 - 35
- E84 - 35
- F01 - 1
- M88 - 16
- C91 - 1
- G41 - 37
- M28 - 35
- G55 - 16
- 20 - 430
- C17 - 3
- M72 - 16
- C45 - 16
- -2
- C19 - 16
- W60 - 50
- 00146 - 2
- 00405 - 2

1710

Missing Admission Hour - Transaction Count = 35

Show [10 ▽] entries                                  Search: [    ]

| Encounter ID ◇ | Status Code ◇ | Response Date ◇ | Response File ◇ | Submitted Date ◇ | |
|---|---|---|---|---|---|
| 14253AA006 | M28 | 5/5/2014 12:00:00 AM | G0051V00-DF.txt | 9/10/2014 12:00:00 AM | Details |
| 14253AA006 | M28 | 5/5/2014 12:00:00 AM | G0051V00-DF.txt | 9/10/2014 12:00:00 AM | Details |
| 14253AA006 | M28 | 5/5/2014 12:00:00 AM | G0051V00-DF.txt | 9/10/2014 12:00:00 AM | Details |
| 14253AA006 | M28 | 5/5/2014 12:00:00 AM | G0051V00-DF.txt | 9/10/2014 12:00:00 AM | Details |
| 14253AA006 | M28 | 5/5/2014 12:00:00 AM | G0051V00-DF.txt | 9/10/2014 12:00:00 AM | Details |
| 14253AA006 | M28 | 5/5/2014 12:00:00 AM | G0051V00-DF.txt | 9/10/2014 12:00:00 AM | Details |
| 14253AA006 | M28 | 5/5/2014 12:00:00 AM | G0051V00-DF.txt | 9/10/2014 12:00:00 AM | Details |
| 14253AA006 | M28 | 5/5/2014 12:00:00 AM | G0051V00-DF.txt | 9/10/2014 12:00:00 AM | Details |

1720

Transaction > Edit

* 837 Encounter P

Encounter Id 14253AA011
Status ADJHOLD

- ⊞ TransactionSetHeader
- ⊞ BeginningOfHierarchicalTransaction
- ⊞ SubmitterName Loop
- ⊞ Receivername
- ⊞ BillingProviderHierarchicalLevel Loop
- ⊞ SubscriberHierarchicalLevel Loop
- ⊞ ClaimInformation Loop
- ⊞ ServiceLineNumber 1
- ⊞ ServiceLineNumber 2
- ⊞ TransactionSetTrailer

1410

Save
Details

Show 10 ▽ entries                                   Search: [    ]

| Review Code | Description | Review Type Desc | Created |
|---|---|---|---|
| 2000APRV03 | Invalid Taxonomy Code | Review | 9/10/2014 11:29:27 AM | Details |
| 2010AANM103 | Billing Provider Validation | Review | 9/10/2014 11:29:27 AM | Details |
| 2010BA103 | Member Validation | Review | 9/10/2014 11:29:27 AM | Details |

Showing 1 to 3 of 3 entries

1420

Response Detail Codes for this Encounter
Create new

Show 10 ▽ entries                                   Search: [    ]

| Encounter ID | Line Number | Category Code | Status Code | Description | Updated By | Updated | | | |
|---|---|---|---|---|---|---|---|---|---|
| 14253AA011 | 1 | Rejected | C91 | Invalid Admit Date for Interim Claim | INVIDASYS\BiztalkHost | 9/11/2014 4:58:24 PM | Details | Edit | Delete |
| 14253AA011 | 3 | Rejected | R17 | Services Invalid For Recipient Age | INVIDASYS\BiztalkHost | 9/11/2014 4:58:24 PM | Details | Edit | Delete |
| 14253AA011 | 4 | Rejected | R17 | Services Invalid For Recipient Age | INVIDASYS\BiztalkHost | 9/11/2014 4:58:24 PM | Details | Edit | Delete |

Showing 1 to 3 of 3 entries

SubmitFiles

Claim Form — 1910
- ○ Dental  ● Institutional  ○ NCPDP  ○ Professional

Submission Type — 1920
- ● Production  ○ Test

Claim Ids — 1930
- ● All Claims
- ○ DOS Range — Dos From [  ]  Dos To [  ]
- ○ Claim Range — Claim Id from [  ]  Claim Id to [  ]
- ○ List of Claim Ids — List of Claim IDs [  ]

Select by — 1940
- Trading Format: [FHP/ACA>APEX>837 Import - Professional]
- Batch size (maximum allowed is 5,000): [  ]
- Claim Type: [Select ▽]

[Submit]

2000 Create Transmission

Claim Ids

⦿ All Claims

○ DOS Range    Dos From [____]    Claim Id from [____]

○ Claim Range    Dos To [____]    Claim Id to [____]

○ List of Claim Ids    List of Claim IDs [____]

— 2010

Select by — 2020

Trading Format

| Select Line Of Business > Trading Partner > Format |
|---|
| Select Line Of Business > Trading Partner > Format |
| CL PACE Dual > CenterLight PACE Dual Eligible > CMS Risk Adjustment Processing System (RAPS) |
| CL PACE Dual > State of New York > New York State Medicaid Encounter Data System (MEDS) III |
| CL PACE Dual > CenterLight PACE Dual Eligible > Medicaid Encounter Data System (MEDS) III - Institutional |
| CL PACE Dual > CenterLight PACE Dual Eligible > Medicaid Encounter Data System (MEDS) III - Professional |
| CL PACE Medicaid > CenterLight PACE Medicaid > Medicaid Encounter Data System (MEDS) III - Institutional |
| CL PACE Medicaid > CenterLight PACE Medicaid > Medicaid Encounter Data System (MEDS) III - Professional |
| CL SELECT LT > CenterLight SELECT LT > Medicaid Encounter Data System (MEDS) III - Institutional |

Batch size (maximum allowed is 5,000)

Claim Type

[Submit]

FIG. 20

ENCOUNTER MANAGEMENT

CROSS-REFERENCE TO RELATED APPLICATION

This application claims the benefit of U.S. Provisional Application No. 62/186,652, filed Jun. 30, 2015. U.S. Provisional Application No. 62/186,652 is incorporated herein by reference in its entirety.

TECHNICAL FIELD

This disclosure relates generally to automated encounter and workflow management, and relates more particularly to managing the flow of work items, such as generating, reviewing, and/or correcting medical encounter transactions.

BACKGROUND

After a health insurance provider has adjudicated and paid a claim, the health insurance provider often seeks reimbursement from Medicare and/or State-based Medicaid systems. The Medicare and State-based Medicaid systems each have their own regulations for encounter submissions and reporting errors. As many as sixty percent of initial encounter submissions for reimbursement do not comply with the regulations and are rejected by the Medicare and/or State-based Medicaid systems due to these errors. Health insurance providers can be penalized for improper and/or late encounter submissions.

Moreover, conventional workflow processing systems typically define the workflow and require that the data fit the workflow. Consequently, costly and time-consuming "rip and replace" procedures are often necessary to update conventional workflow processing systems in order to handle new or modified transactions or data formats.

BRIEF DESCRIPTION OF THE DRAWINGS

To facilitate further description of the embodiments, the following drawings are provided in which:

FIG. 5 illustrates an exemplary user interface display of the management application, showing a form for editing data rules, specifically an update rule;

FIG. 6 illustrates an exemplary user interface display of the management application, showing a form for editing data rules, specifically a filter rule;

FIG. 9 illustrates an exemplary user interface display of the management application, showing a list of data dictionary schema that are supported by the management application on the management system of FIG. 1;

FIG. 10 illustrates an exemplary user interface display of the management application, showing a dashboard of workflow transaction activity;

FIG. 11 illustrates an exemplary user interface display of the management application, showing a list of data records defined by an individual grouping in the dashboard of the user interface display of FIG. 10;

FIG. 12 illustrates an exemplary user interface display of the management application, showing a list of queues for an exemplary transaction type;

FIG. 13 illustrates an exemplary user interface display of the management application, showing a list of users assigned to roles;

FIG. 14 illustrates an exemplary user interface display of the management application, showing a form for editing an individual data record;

FIG. 15 illustrates an exemplary user interface display of the management application, showing a form for reviewing an individual data record that has a duplicate entry;

FIG. 16 illustrates an exemplary user interface display of the management application, showing a list of status codes;

FIG. 17 illustrates an exemplary user interface display of the management application, showing a list of response queues corresponding to status codes and a list of data records that are assigned to one of the response queues in list of response queues;

FIG. 18 illustrates an exemplary user interface display of the management application, showing a form for reviewing an individual data record and the status codes under which the individual data records was rejected;

FIG. 19 illustrates an exemplary user interface display of the management application, showing a form for submitting a file to a governmental entity of FIG. 1 for data records that are ready for submission;

FIG. 20 illustrates an exemplary user interface display of the management application, showing a form for creating transactions for submission to the governmental entity of FIG. 1 in different format;

Figure 1:
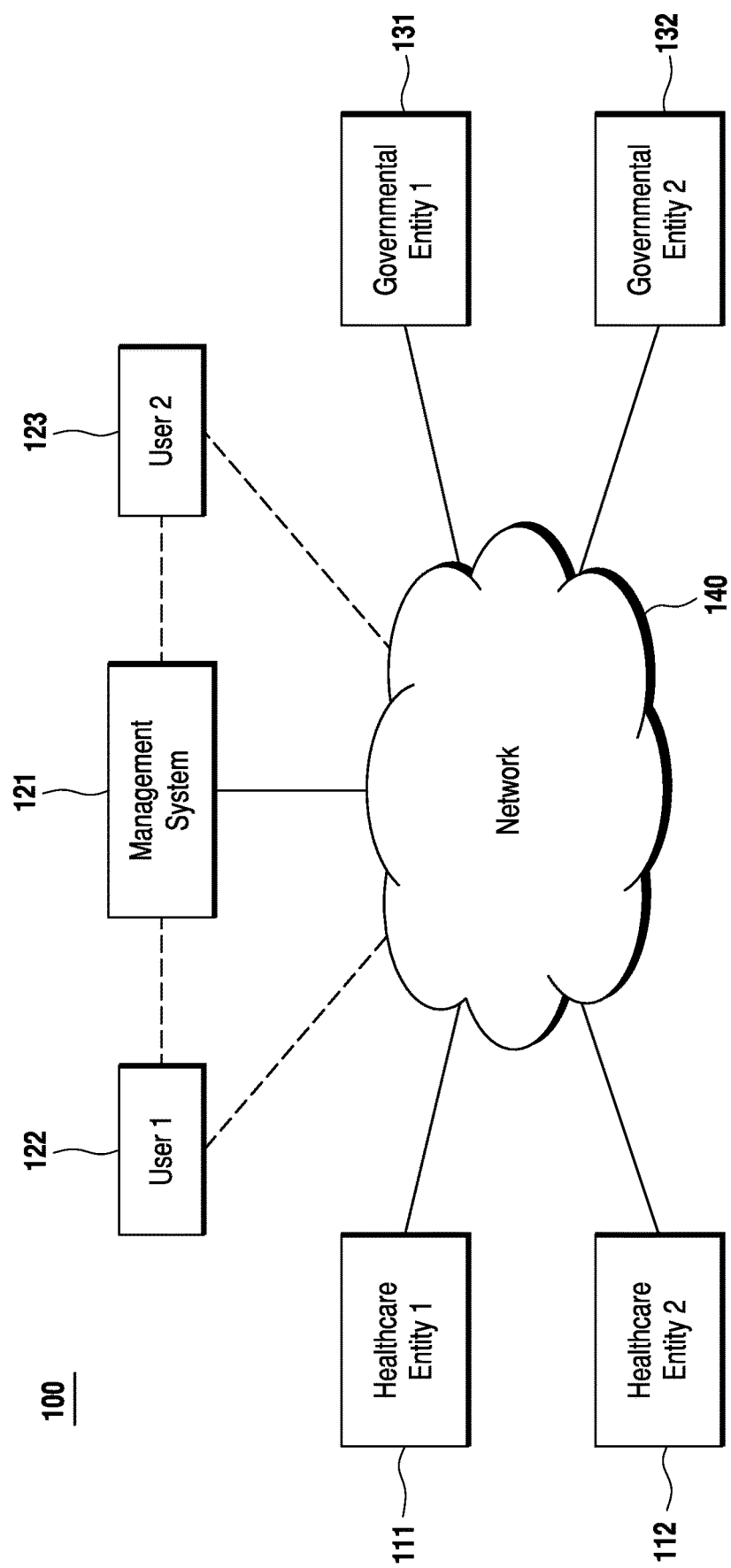
FIG. 1 illustrates a block diagram of a system that can be employed for encounter management and/or workflow management, according to an embodiment.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent or semi-permanent or only for an instant. "Electrical coupling" and the like should be broadly understood and include electrical coupling of all types. The absence of the word "removably," "removable," and the like near the word "coupled," and the like does not mean that the coupling, etc. in question is or is not removable.

As defined herein, two or more elements are "integral" if they are comprised of the same piece of material. As defined herein, two or more elements are "non-integral" if each is comprised of a different piece of material.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

DESCRIPTION OF EXAMPLES OF EMBODIMENTS

Various embodiments include a method for encounter management. The method can be implemented via execution of computer instructions configured to run at one or more processing modules and configured to be stored at one or more non-transitory memory storage modules. The method can include receiving one or more encounters to be submitted to one or more governmental entities for reimbursement after the encounters have been adjudicated and paid by a health insurance plan. Each of the one or more encounters can represent a claim for reimbursement for a medical encounter. The method also can include verifying whether each of the one or more encounters comply with regulations specified by the one or more governmental entities to determine one or more improper encounters of the one or more encounters comprising one or more errors that do not comply with the regulations specified by the one or more governmental entities. The method further can include correcting the one or more improper encounters of the one or more encounters to comply with the regulations specified by the one or more governmental entities. The method additionally can include submitting the one or more encounters, including the one or more improper encounters, as corrected, to the one or more governmental entities for reimbursement. The method further can include receiving one or more responses from the one or more governmental entities corresponding to the one or more encounters.

A number of embodiments include a system for encounter management. The system can include one or more processing modules and one or more non-transitory memory storage modules storing computing instructions configured to run on the one or more processing modules and perform various acts. The acts can include receiving one or more encounters to be submitted to one or more governmental entities for reimbursement after the encounters have been adjudicated and paid by a health insurance plan. Each of the one or more encounters can represent a claim for reimbursement for a medical encounter. The acts also can include verifying whether each of the one or more encounters comply with regulations specified by the one or more governmental entities to determine one or more improper encounters of the one or more encounters comprising one or more errors that do not comply with the regulations specified by the one or more governmental entities. The acts further can include correcting the one or more improper encounters of the one or more encounters to comply with the regulations specified by the one or more governmental entities. The acts additionally can include submitting the one or more encounters, including the one or more improper encounters, as corrected, to the one or more governmental entities for reimbursement. The acts further can include receiving one or more responses from the one or more governmental entities corresponding to the one or more encounters.

Additional embodiments can include a method for workflow management. The method can be implemented via execution of computer instructions configured to run at one or more processing modules and configured to be stored at one or more non-transitory memory storage modules. The method can include receiving a plurality of data records from one or more sources. Each data record of the plurality of data records can include a data format. Each data record of the plurality of data records can include a transaction type. The method also can include processing a plurality of steps for each data record of the plurality of data records. The plurality of steps processed for each data record of the plurality of data records can differ depending on the transaction type of the data record. One or more of the plurality of steps can interface with each data record of the plurality of data records based on a data dictionary schema corresponding to the data format of the data record. One or more first steps of the plurality of steps can be configured to conditionally add one or more first data records of the plurality of data records to one or more queues for manual processing. The method further can include adding the one or more first data records of the plurality of data records to the one or more queues for manual processing. Each of the one or more first data records of the plurality of data records can be added to one or more of the one or more queues based on one or more exception conditions being satisfied in one or more of the one or more first steps of the plurality of steps. The plurality of steps processed for each transaction type and the one or more queues for manual processing can be customizable by a user.

Further embodiments include a system for workflow management. The system can include one or more processing modules and one or more non-transitory memory storage modules storing computing instructions configured to run on the one or more processing modules and perform various acts. The acts can include receiving a plurality of data records from one or more sources. Each data record of the plurality of data records can include a data format. Each data record of the plurality of data records can include a transaction type. The acts also can include processing a plurality of steps for each data record of the plurality of data records. The plurality of steps processed for each data record of the plurality of data records can differ depending on the transaction type of the data record. One or more of the plurality of steps can interface with each data record of the plurality of data records based on a data dictionary schema corresponding to the data format of the data record. One or more first steps of the plurality of steps can be configured to conditionally add one or more first data records of the plurality of data records to one or more queues for manual processing. The acts further can include adding the one or more first data records of the plurality of data records to the one or more queues for manual processing. Each of the one or more first data records of the plurality of data records can be added to one or more of the one or more queues based on one or more exception conditions being satisfied in one or more of the one or more first steps of the plurality of steps. The plurality of steps processed for each transaction type and the one or more queues for manual processing can be customizable by a user.

Turning to the drawings, FIG. 1 illustrates a block diagram of a system 100 that can be employed for encounter management and/or workflow management, according to an embodiment. System 100 is merely exemplary, and embodiments of the system are not limited to the embodiments presented herein. The system can be employed in many different embodiments or examples not specifically depicted or described herein. In some embodiments, certain elements or modules of system 100 can perform various procedures, processes, and/or activities. In other embodiments, the procedures, processes, and/or activities can be performed by other suitable elements or modules of system 100. In many embodiments, system 100 can include one or more healthcare entities (e.g., 111, 112). Healthcare entities 111-112 each can include a single computer, a single server, a cluster or collection of computer or servers, or a cloud of computer or servers. Healthcare entities 111-112 can each be a healthcare entity, such as a health insurance plan, a healthcare provider, a medical claims clearinghouse, or another suitable healthcare entity.

In several embodiments, system 100 can include a management system 121, which can be a single computer, a single server, a cluster or collection of computer or servers, or a cloud of computer or servers. In a number of embodiments, system 100 can include one or more governmental entities (e.g., 131, 132). Governmental entities 131-132 each can include a single computer, a single server, a cluster or collection of computer or servers, or a cloud of computer or servers. Governmental entities 131-132 can each be a governmental entity that handles reimbursement of medical claims, such as the Centers for Medicare & Medicaid Services (CMS) or a State-based Medicaid entity, such as the New York State Department of Health.

In many embodiments, healthcare entities 111-112 and governmental entities 131-132 can be in data communication with management system 121 through a network 140. Network 140 can be a local area network (LAN), a wireless LAN, a wide area network (WAN), a mobile telecommunications wireless data network, the Internet, another suitable network, or a combination thereof. In certain embodiments, management system 121 can facilitate certain communications between healthcare entities 111-112 and governmental entities 131-132.

In several embodiments, management system 121 can present a user interface to one or more users (e.g., 122, 123) of one or more management applications, such as an encounter management application, a workflow management application, and/or other applications. In a number of embodiments, the applications can be separate applications. In other embodiments, the applications can be integrated as a single application. In many embodiments, management system 121 can present the management application to the users (e.g., 122-123) through a network-based service through network 140, such as through a web browser, such as on a visual display of a device used by the user (e.g., 122-123). In other embodiments, one or more users (e.g., 122-123) can access the management application by interfacing directly with management system 121, such as through display and/or input devices of management system 121.

In many embodiments, management system 121 can be used to manage the flow of work items. In several embodiments, management system 121 can automate the flow of tasks, information, or documents based on a predetermined set of rules, which can beneficially streamline business processes. In many embodiments, management system 121 can extend and enhance the functionality of existing systems in an agile and scalable manner. In several embodiments, management system 121 can be configured such that the transactions can define the workflow.

In some embodiments, management system 121 can be used to validate and/or generate compliant medical encounter transactions. For example, a healthcare entity (e.g., 111-112), such as a health insurance plan, can adjudicate and pay a claim, and then seek reimbursement from a governmental entity (e.g., 131-132), such as CMS for Medicare claims, and/or a State-based Medicaid system for Medicaid claims. Governmental entities (e.g., 131-132), such as CMS and State-based Medicaid systems, generally each have their own regulations for encounter submissions, and they generally will reject encounter submissions that do not comply with the regulations. Improper submissions that are rejected can result in penalties and/or the need to correct and resubmit the improper submissions. These resubmissions can be submitted late (such as more than 30 days after the date of service), especially if the submissions need to be resubmitted multiple times, which can result in additional penalties. In many embodiments, management system 121 can validate each encounter prior to submission to greatly reduce the likelihood of rejections from the governmental entity (e.g., 131-132). For example, management system 121 can automatically correct various errors, and for errors that require manual correction, can add the encounter submissions to one or more queues for manual correction.

In many embodiments, the flow of work for the encounter submission can be determined based on the transaction. For example, management system 121 can process institutional medical encounter submission for Medicare reimbursement through a different workflow than a professional medical encounter submission for Medicaid reimbursement through the New York State Department of Health. Additionally, different format types can be required by the governmental entities (e.g., 131-132), such as HIPAA-compliant EDI (electronic data interchange) X12N 837 version 5010 format, which can include different formats for 837I (institutional), 837P (professional), and 837D (dental) encounters, or the MEDS (Medicaid Encounter Data System) III format.

For each transaction type and format, the regulations can specify a number of data requirements for the submission to be compliant. For example, certain types of encounters in Illinois involving an ambulance can require that the license plate number of the ambulance be included in the data submission. If the required data is missing, the encounter submission can be rejected by the governmental entity (e.g., 131-132). As another example, each State can have a list of valid providers, and the name of the provider can need to be spelled in the exact same way as it is provided in the list of valid providers, or the encounter submission can be rejected by the governmental entity (e.g., 131-132).

In several embodiments, management system 121 can manage responses received from the governmental entity (e.g., 131-132). For example, management system 121 can determine the rejected encounter submissions and can add the rejected encounter submissions to one or more queues for manual correction, based on the one or more rejection types.

Although management system 121 is described herein as managing the flow of work items in the context of generating compliant medical encounter transactions, it can be appreciated that management system 121 can advantageously be used to manage the flow of work items in many other contexts.

In several embodiments, management system 121 can receive data files from the healthcare entities (e.g., 111-112), which can include sources of data records. For example, a data file can include a number of 837I records in a flat data file. In some embodiments, the data records can be converted to a markup language format, such as XML (Extensible Markup Language) based on a data dictionary schema for the format of the data records, which can generate a data structure for each of the data records, and which can facilitate processing operations on the data records. In a number of embodiments, the data records can be converted back to records (e.g., 837I, MEDS III, etc.) in a flat data file for submission to the governmental entities (e.g., 131-132). In converting the data records to XML, in several embodiments, management system 121 can validate whether required segments for the data format are included and/or that the segments have the correct length. In some embodiments, the data dictionary schema can specify that if a certain field exists, then another field is required to exist, and management system 121 can ensure that the data records satisfy that data taxonomy specified by the data dictionary schema.

Figure 2:
FIG. 2 illustrates an exemplary user interface display of the management application provided by the management system of FIG. 1, showing a list of steps of a workflow for an exemplary transaction type of a source.

Turning ahead in the drawings, FIG. 2 illustrates an exemplary user interface display 200 of the management application, showing a list of steps 220 of a workflow for an exemplary transaction type of a source 210. User interface display 200 is merely exemplary, and embodiments of the management application can be employed in many different embodiments or examples not specifically depicted or described herein. As shown in FIG. 2, source 210 of data records can be institutional encounter claims for the State of Illinois, and list of steps 220 can include a number of steps that provide a workflow for validating the data records in source 210. The steps in list of steps 220 can be executed by management system 121 (FIG. 1) in validating institution claims for the State of Illinois. The steps executed for validating of types of claims (e.g., professional claims for the State of Illinois, institutional claims for CMS) can be different. In many embodiments, the transaction type can define the workflow executed by management system 121 (FIG. 1).

In a number of embodiments, each step of list of steps 220 can be executed by management system 121 (FIG. 1) against the data records. In many embodiments, each step can perform an operation to validate and/or correct each of the data records. The steps in list of steps can be executed in the order indicated in the transaction sequence number of list of steps 220. The sequence name of list of steps 220 can provide a brief description of the step. In a number of embodiments, one or more of the steps can perform a validation operation against each data record. If the data record fails the validation operation, the step can assign a review code to allow the data record to be manually reviewed. The review codes can be listed in the step action of list of steps 220. In a number of embodiments, when a validation operation fails, the step can add the data record to a queue for manual review. The queue name of list of steps 220 can provide a queue name for the assigned queue. In several embodiments, a data record can be added to one or more queues as the steps in list of steps 220 are executed against the data record.

For example, step 13 in list of steps 220 has a sequence name "Billing—Illinois Verify Provider," which can be used to validate that the National Provider Identifier (NPI) is a provider in the provider database for the State of Illinois. If the validation fails, step 13 can assign the review code of "BILLNOFIX," and assign the data record to the "NPI Issues" queue.

As another example, step 11 in list of steps 220 has a sequence name "Subscriber—Update SBR01 Validation," which can be used to ensure that a certain SBR01 segment of the encounter submission is populated with the correct data. Step 11 can automatically correct the data to ensure that the relevant segment is correct. As such, step 11 can automatically correct the data and without ever assigning a review code.

In several embodiments, the steps to be executed in a workflow by management system 121 (FIG. 1) can be modified. For example, the steps in list of steps 220 can be edited, new steps can be added, and/or existing steps can be deleted.

Figure 3:
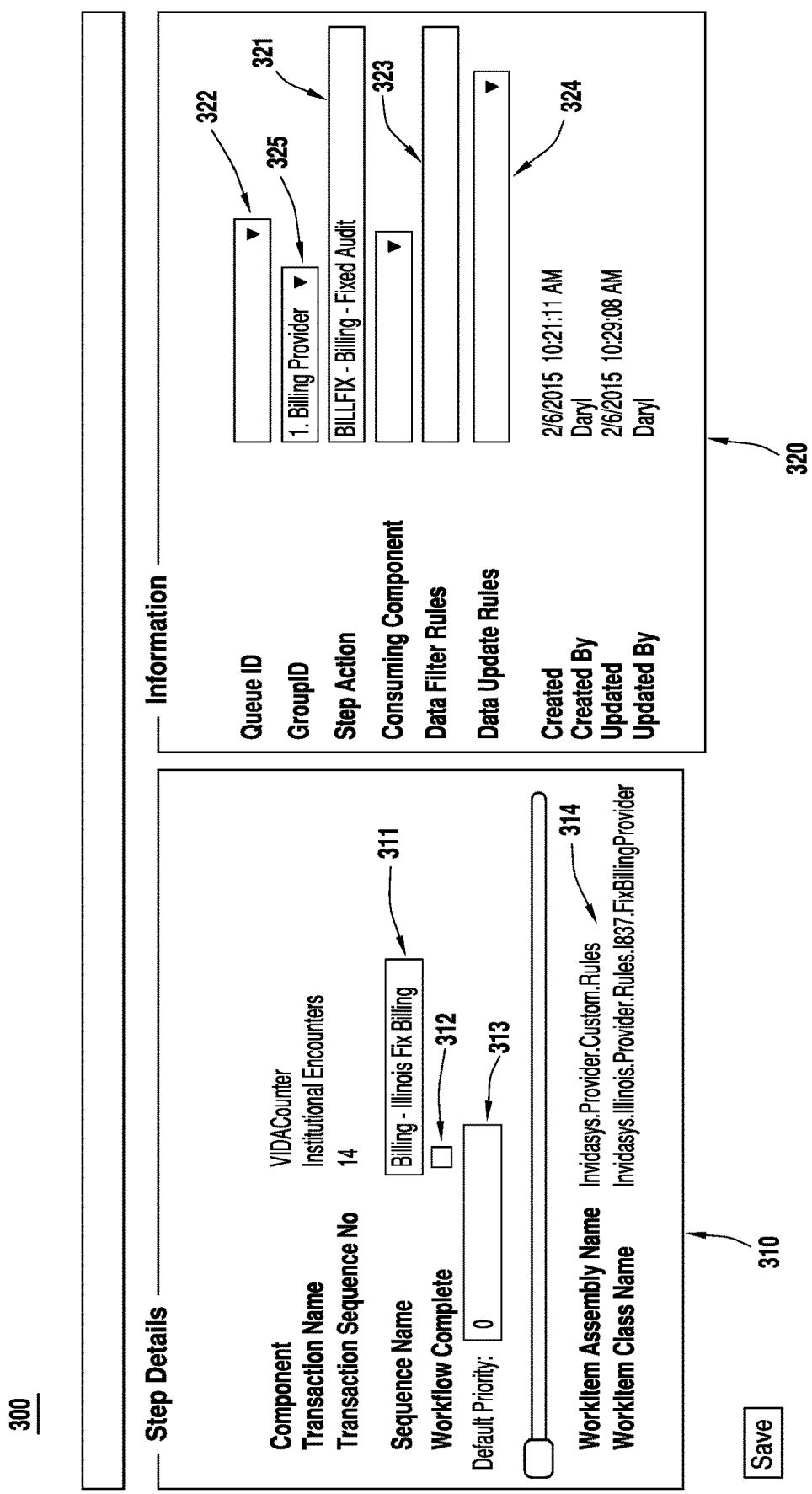
FIG. 3 illustrates an exemplary user interface display of the management application, showing a form for editing an individual step of the list of steps of FIG. 2.

Turning ahead in the drawings, FIG. 3 illustrates an exemplary user interface display 300 of the management application, showing a form for editing an individual step, specifically a step 14, of list of steps 220 (FIG. 2). User interface display 300 is merely exemplary, and embodiments of the management application can be employed in many different embodiments or examples not specifically depicted or described herein. Management system 121 (FIG. 1) can provide user interface display 300 to a user (e.g., 122-123 (FIG. 1)) to create or modify a step.

As shown in FIG. 3, step 14 can be modified or otherwise defined using user interface display 300. In many embodiments, user interface display 300 can include step details 310 and step information 320. In some embodiments, for example, the user (e.g., 122-123 (FIG. 1)) can enter and/or modify a sequence name of "Billing—Illinois Fix Billing" in a sequence name field 311. In several embodiments, the user (e.g., 122-123 (FIG. 1)) can designate the step as completing the workflow in a workflow complete field 312. In various embodiments, the user (e.g., 122-123 (FIG. 1)) can designate a default priority for the step in a default priority field 313. In many embodiments, the user (e.g., 122-123 (FIG. 1)) can designate an assembly in assembly fields 314. For example, the assembly can be code, such as custom code, for the step to execute a custom-developed rule. As shown in FIG. 3, step 14 can execute custom code to fix the billing provider.

In a number of embodiments, the user (e.g., 122-123 (FIG. 1)) can designate a review code, such as "BILLFIX," in step action field 321. In several embodiments, the review code can be assigned if the validation executed by the assembly fails. In a number of embodiments, the user (e.g., 122-123 (FIG. 1)) can designate a queue in a queue field 322, which can put data records in a queue if when the data record fails the validation. In some embodiments, the user (e.g., 122-123 (FIG. 1)) can designate a filter rule in a filter rule field 323. In various embodiments, the user (e.g., 122-123 (FIG. 1)) can designate an update rule in an update rule field 324. In many embodiments, the update rule can specify segments of the data to update (such as add, modify, or delete). In many embodiments, the update rule can be applied to a data record only if the data record qualifies under the filter rule. In various embodiments, the step can be categorized in a group, which can be designated and/or updated in a group ID field 325. For example, step 14 can be categorized in a "Billing Provider" group of steps.

Figure 4:
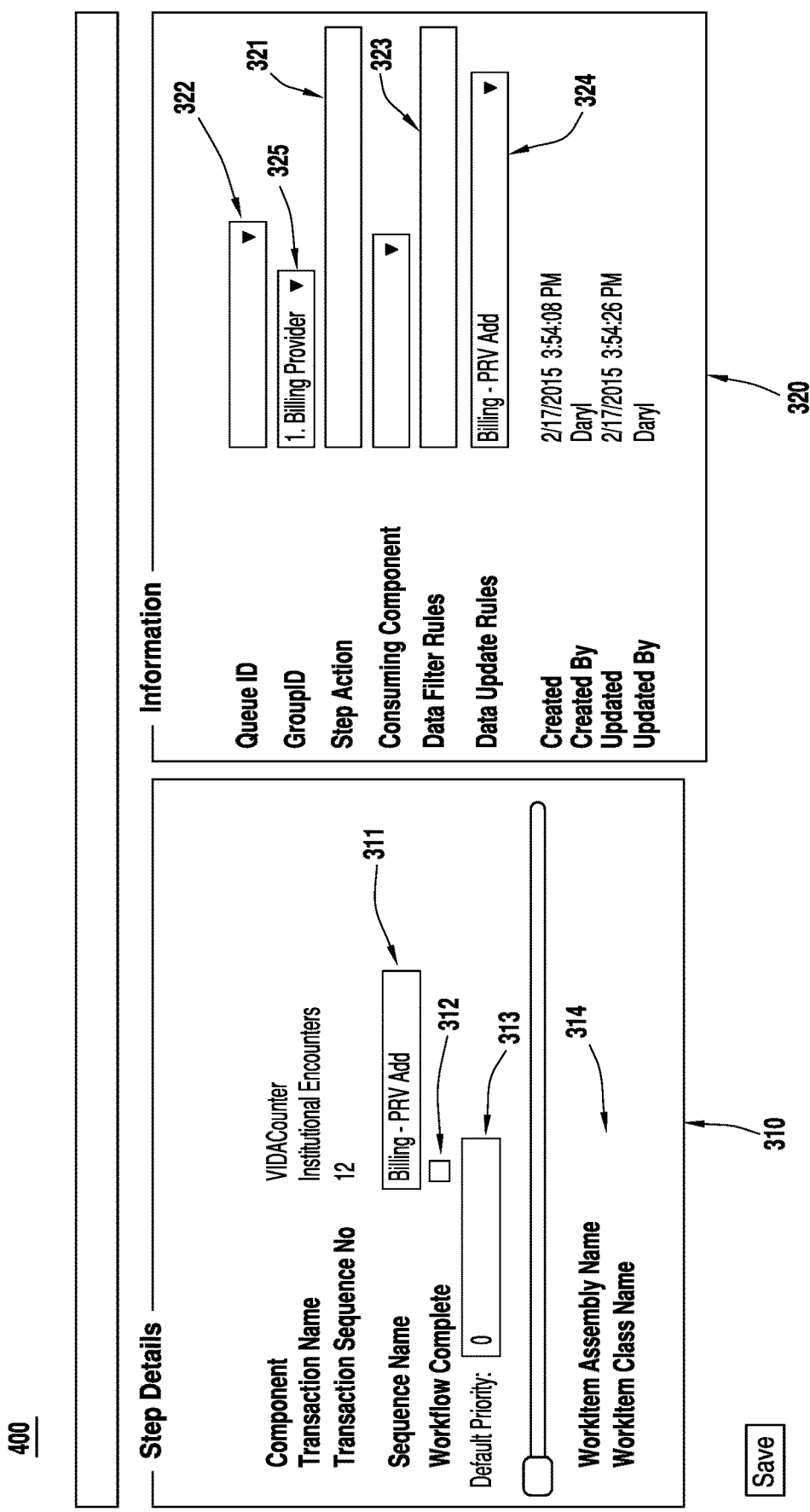
FIG. 4 illustrates an exemplary user interface display of the management application, showing a form for editing a different individual step of list of steps of FIG. 2.

Turning ahead in the drawings, FIG. 4 illustrates an exemplary user interface display 400 of the management application, showing a form for editing an individual step, specifically a step 12, of list of steps 220 (FIG. 2). User interface display 400 is merely exemplary, and embodiments of the management application can be employed in many different embodiments or examples not specifically depicted or described herein. User interface display 400 can be similar to user interface display 300 (FIG. 3), and various elements of user interface display 400 can be similar or identical to various elements of user interface display 300 (FIG. 3). For example, user interface display 400 can include step details 310 and step information 320.

As shown in FIG. 4, step 12 can be modified or otherwise defined using user interface display 400. Step 12 can be designated in sequence name field 311 as having a sequence name of "Billing—PRV Add," and instead of having a custom assembly designated in assembly field 314, step 12 can designate an update rule of "Billing—PRV Add" in update rule field 324, which can modify the data records that are run against step 12. In several embodiments, because step 12 does not designate a field rule in filter rule field 324, step 12 can apply the update rule to all of the data records that are run against step 12, rather than just the data records that qualify under the filter rule.

In some embodiments, for example, the user (e.g., 122-123 (FIG. 1)) can enter and/or modify a sequence name of "Billing—Illinois Fix Billing" in a sequence name field 311. In several embodiments, the user (e.g., 122-123 (FIG. 1)) can designate the step as completing the workflow in a workflow complete field 312. In various embodiments, the user (e.g., 122-123 (FIG. 1)) can designate a default priority for the step in a default priority field 313. In many embodiments, the user (e.g., 122-123 (FIG. 1)) can designate an assembly in assembly fields 314. For example, the assembly can be code, such as custom code, for the step to execute a custom-developed rule. As shown in FIG. 3, step 14 can execute custom code to fix the billing provider.

Turning ahead in the drawings, FIG. 5 illustrates an exemplary user interface display 500 of the management application, showing a form for editing data rules, specifically an update rule. User interface display 500 is merely exemplary, and embodiments of the management application can be employed in many different embodiments or examples not specifically depicted or described herein. Management system 121 (FIG. 1) can provide user interface display 500 to a user (e.g., 122-123 (FIG. 1)) to create or modify a data rule, such as an update rule or a filter rule.

As shown in FIG. 5, a descriptor of the data rule can be specified in a filter name field 511. For example, the descriptor for the update rule, "Billing—PRV Add," can be included in filter name field 511. In many embodiments, update rule "Billing—PRV Add" can be modified or otherwise defined using user interface display 500. In many embodiments, user interface display 500 can include an update filter designation field 512, which can designate whether or not the data rule is an update rule, or instead, a filter rule. Because update filter designation field 512 is set to true, "Billing—PRV Add" is an update rule.

In many embodiments, user interface display 500 can include rule details 513. In several embodiments, the user (e.g., 122-123 (FIG. 1)) can enter and/or modify rule details 513 to specify how the update rule "Billing—PRV Add" will create and/or update data elements in the data record. For example, an update rule can create one or more data segments and/or one or more elements within the data segments. In the same or other examples, an update rule can modify and/or trim one or more data segments and/or one or more elements within the data segments. In the same or other examples, an update rule can delete one or more data segments and/or one or more elements within the data segments. For example, the update rule "Billing—PRV Add" can be used by step 12 in FIG. 4 to update every encounter with data points required by the State of Illinois for 837I encounter submissions.

Management system 121 (FIG. 1) advantageously can be configured correct data compliance errors using update rules and/or assemblies in steps, such as steps in list of steps 220 (FIG. 2). For example, an incoming 837I encounter submission can include data fields that specify a doctor as the submitter and a healthcare insurance provider as the receiver. When submitting the encounter to the New York State Department of Health as a MEDS III, the data fields need to be updated such that the submitter is changed to the healthcare insurance provider, which was the receiver in the original submission. In many embodiments, each of the updates made by the update rules and/or assemblies can be logged to create an audit record of the data records that were changed and the update rules and/or assemblies that changed the data records.

Turning ahead in the drawings, FIG. 6 illustrates an exemplary user interface display 600 of the management application, showing a form for editing data rules, specifically a filter rule. User interface display 600 is merely exemplary, and embodiments of the management application can be employed in many different embodiments or examples not specifically depicted or described herein. User interface display 600 can be similar to user interface display 500 (FIG. 5), and various elements of user interface display 600 can be similar or identical to various elements of user interface display 500 (FIG. 5). For example, user interface display 600 can include filter name field 511, update filter designation field 512, and rule details 513.

As shown in FIG. 6, a descriptor for the filter rule, "Principal Diag POA Indicator" can be included in filter name field 511. In many embodiments, filter rule "Principal Diag POA Indicator" can be modified or otherwise defined using user interface display 600. Update filter designation field 512, can designate that the data rule is not update rule, but instead a filter rule, because update filter designation field 512 is set to false.

In several embodiments, the user (e.g., 122-123 (FIG. 1)) can enter and/or modify rule details 513 to specify how the filter rule "Principal Diag POA Indicator" will conditionally qualify the data record to apply an update rule. For example, a filter rule can determine whether a data element of a data segment equals a specified value, is not equal to a specified value, is less than a specified value, is greater than a specified value, begins with a specified value, ends with a specified value, contains a specified value, does not contain a specified value, exists, is missing, has a length equal to a specified value, has a length greater than a specified value, has a length less than a specified value, etc. In a number of embodiments, each condition can be combined in a logical conjunction or disjunction. If a data record is qualified under the filter rule, management system 121 can apply the update rule associated in the step (e.g., an update rule in update rule field 324 (FIGS. 3-4) that is associated with a filter rule in filter rule field 323 (FIGS. 3-4)).

Figure 7:
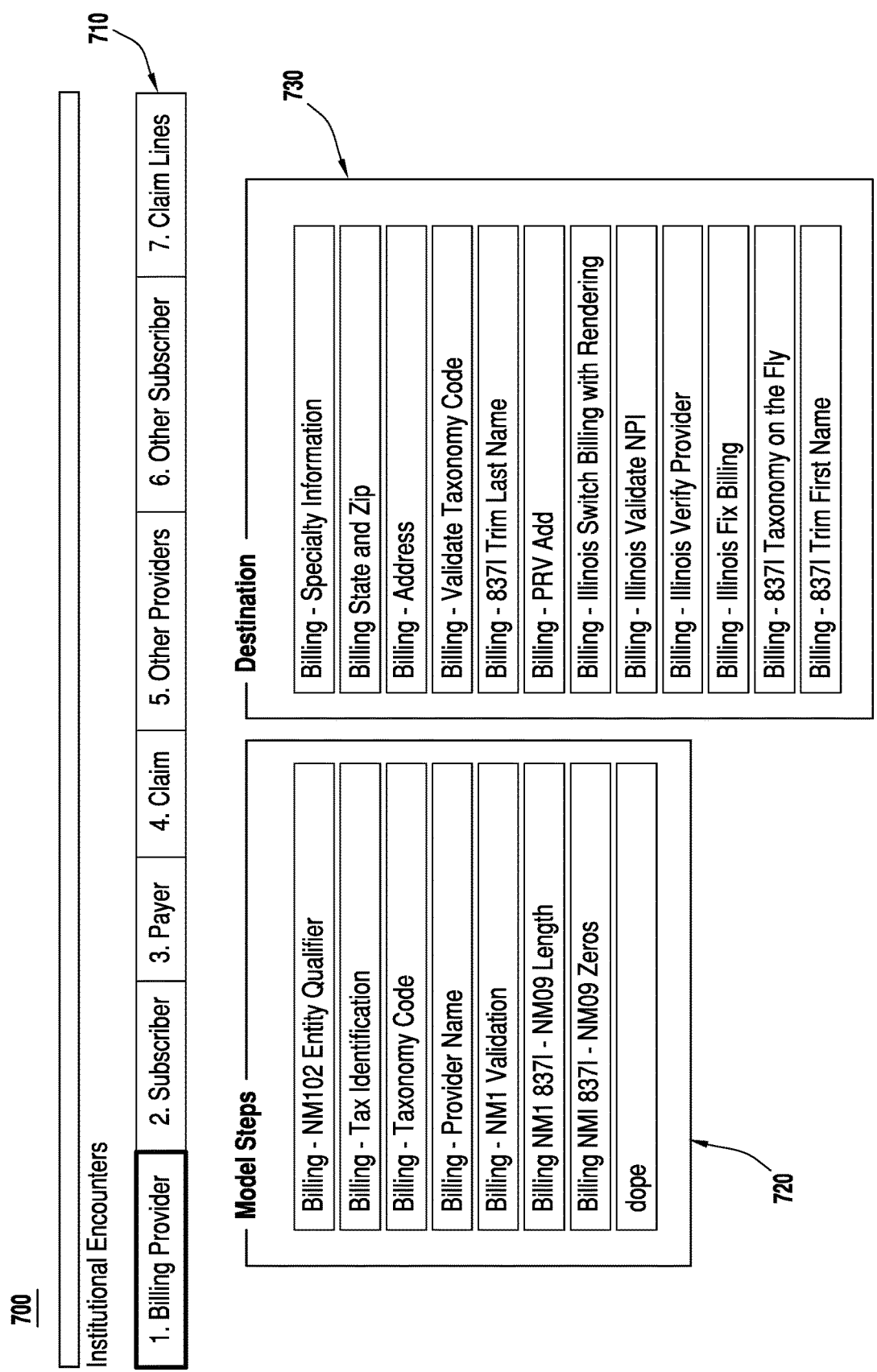
FIG. 7 illustrates an exemplary user interface display of the management application, showing adding rules to a workflow.

Turning ahead in the drawings, FIG. 7 illustrates an exemplary user interface display 700 of the management application, showing adding rules to a workflow. User interface display 700 is merely exemplary, and embodiments of the management application can be employed in many different embodiments or examples not specifically depicted or described herein. Management system 121 (FIG. 1) can provide user interface display 700 to a user (e.g., 122-123 (FIG. 1)) to add default and/or custom rules to a workflow.

Figure 8:
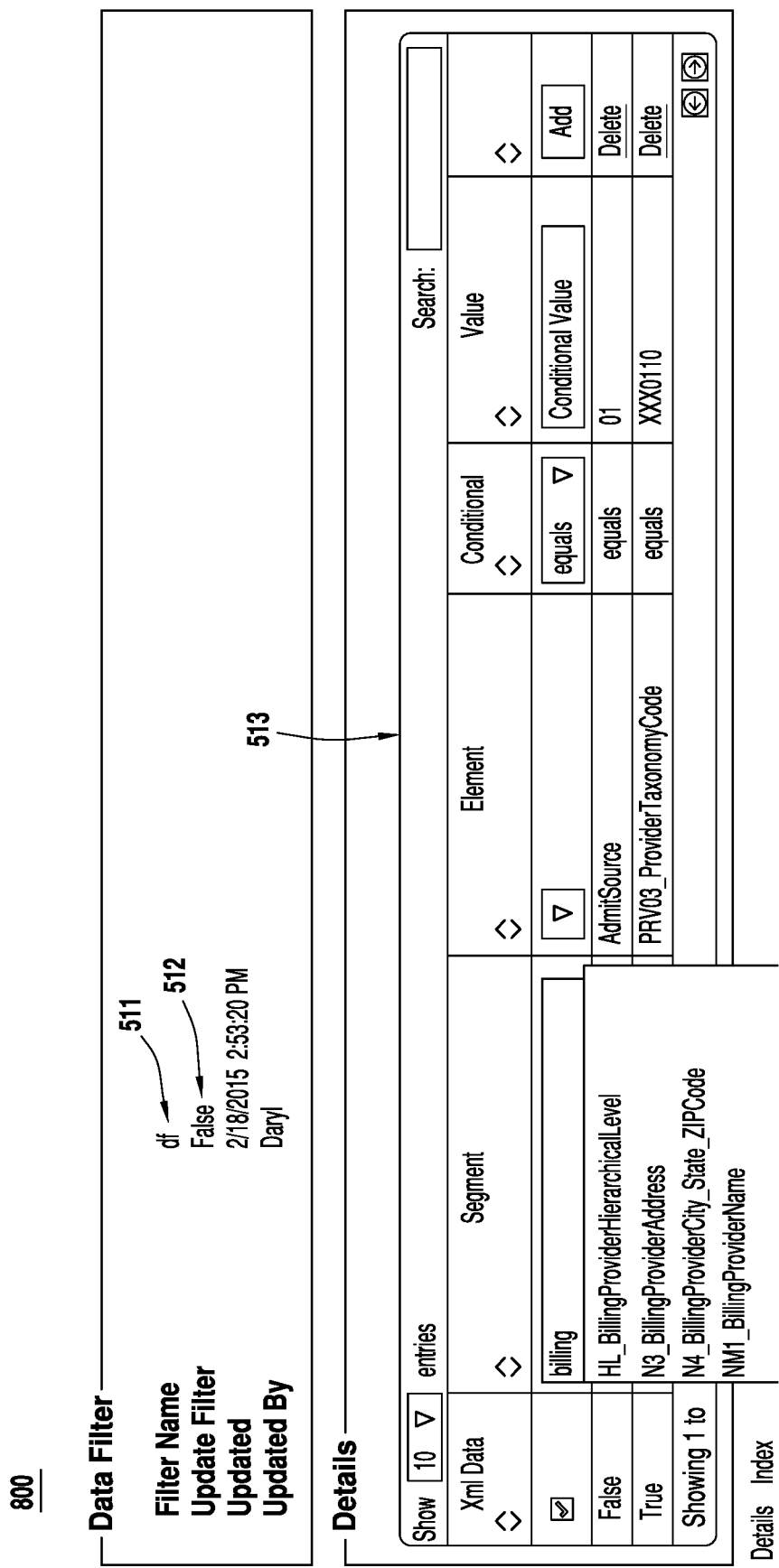
FIG. 8 illustrates an exemplary user interface display of the management application, showing a form for editing data rules, specifically to create a filter rule.

In many embodiments, user interface display 700 can display the steps by groups 710, such as billing provider steps, subscriber steps, payer steps, claim steps, other providers steps, other subscriber steps, claim lines steps, etc. In a number of embodiments, each group can be displayed when selected. As shown in FIG. 7, the billing provider steps are selected from groups 710, so as to display the billing provider steps. In several embodiments, user interface display 700 can include model steps 720 and destination steps 730. Model steps 720 can include default steps in the billing provider group that are available to be added to the workflow. Destination steps 730 can list the steps in the billing provider group that are included in the current workflow, which in this example is a workflow for institutional encounters for the State of Illinois. In various embodiments, new steps can be created, such as shown in FIG. 8, described below. In a number of embodiments, a single step can be reused in multiple different workflows.

Turning ahead in the drawings, FIG. 8 illustrates an exemplary user interface display 800 of the management application, showing a form for editing data rules, specifically to create a filter rule. User interface display 800 is merely exemplary, and embodiments of the management application can be employed in many different embodiments or examples not specifically depicted or described herein. User interface display 800 can be similar to user interface display 500 (FIG. 5) and/or user interface display 600 (FIG. 6), and various elements of user interface display 800 can be similar or identical to various elements of user interface display 500 (FIG. 5) and/or user interface display 600 (FIG. 6). For example, user interface display 800 can include filter name field 511, update filter designation field 512, and rule details 513. Management system 121 (FIG. 1) can provide user interface display 800 to a user (e.g., 122-123 (FIG. 1)) to create a custom rule, which can be added to a workflow.

As shown in FIG. 8, the user (e.g., 122-123 (FIG. 1)) can enter a descriptor for the custom rule, such as "df" in filter name field 511. Update filter designation field 512, can be used to designate whether the data rule is an update rule. As shown in FIG. 8, the custom rule is a filter rule, not an update rule, because update filter designation field 512 is set to false.

In several embodiments, the user (e.g., 122-123 (FIG. 1)) can enter and/or modify rule details 513 to specify how the filter rule "df" will conditionally qualify data records to apply an update rule. For example, the user (e.g., 122-123 (FIG. 1)) can enter one or more segments and/or elements of the data records for conditional qualification. The segments and/or elements of the data records can be defined by the XML data structure taxonomy, which can be based on the data dictionary schema for the data format type.

Turning ahead in the drawings, FIG. 9 illustrates an exemplary user interface display 900 of the management application, showing a list of data dictionary schema 910 that are supported by the management application on management system 121 (FIG. 1). User interface display 900 is merely exemplary, and embodiments of the management application can be employed in many different embodiments or examples not specifically depicted or described herein. Management system 121 (FIG. 1) can provide user interface display 900 to a user (e.g., 122-123 (FIG. 1)) to create, modify, or delete data dictionary schema.

Management system 121 (FIG. 1) can support a number of different data dictionary schema, as shown in list of data dictionary schema 910. The data dictionary schema in list of data dictionary schema 910 can be used by to define the data structure of data records (e.g., the XML data structure), such that management system 121 can modify data dynamically for each of the supported formats. For example, management system 121 can support data records from various sources in a number of different formats using various different data dictionary schema, such as various MEDS III formats (e.g., dental, institutional, pharmacy, professional), various HIPAA-compliant EDI X12 version 5010 formats, such as 837D, 837I, 837P, 835, 834, 277, 276, and various other data formats. Management system 121 (FIG. 1) advantageously can allow a data format, such as 837I, to be processed by different rules for different types of transactions (e.g., CMS, State of Illinois, etc.), but to use the same data dictionary schema.

Turning ahead in the drawings, FIG. 10 illustrates an exemplary user interface display 1000 of the management application, showing a dashboard of workflow transaction activity. User interface display 1000 is merely exemplary, and embodiments of the management application can be employed in many different embodiments or examples not specifically depicted or described herein. Management system 121 (FIG. 1) can provide user interface display 1000 to a user (e.g., 122-123 (FIG. 1)) to display workflow transaction activity and queues. In a number of embodiments, user interface display can display workflow transaction activity and queues by transaction type, such as by separating institutional encounters, professional encounters, dental encounters, etc.

As shown in FIG. 10, the dashboard in user interface display 1000 can include a list of queues 1010 for institutional encounters. In a number of embodiments, list of queues 1010 can include queues that are defined for a transaction type, such as the queues shown in FIG. 12, described below. A user (e.g., 122-123 (FIG. 1)) can select a queue in list of queues 1010 to provide manual corrections to data records that were added to the queue. For example, the "NPI Issues" queue in list of queues 1010 can include all data records that have open NPI-type review codes. The user (e.g., 122-123 (FIG. 1)) can select the "NPI Issues" queue to work on data records in the "NPI Issues" queue that need manual correction or to view information regarding those data records.

In some embodiments, each queue in list of queues 1010 can include a usage depiction bar to indicate the number of data records in the queue. In a number of embodiments, the threshold for a full queue can be set dynamically for each queue based on how many data records are expected to be in the queue. For example, one queue can have a full usage depiction bar when there are 20 data records in the queue, while another queue can have a full usage depiction bar when there are 1000 data records in the queue.

In a number of embodiments, the dashboard in user interface display 1000 can include a list of trends 1020. For example, list of trends 1020 can show activity for open items, such as how may data records are manually processed, during a period of time, such as during today and during each of the last seven days. In many embodiments lists of trends 1020 can beneficially provide a simple summary of the amount of work being accomplished by users in manually addressing open issues with data records. In several embodiments, a user (e.g., 122-123 (FIG. 1)) can select a trend in list of trends 1020 to view information regarding those data records.

In various embodiments, the dashboard in user interface display 1000 can include a list of aging information 1030. For example, list of aging information 1030 can show how long data records with open issues that need to be manually addressed have been in the workflow process. As shown in FIG. 10, in some embodiments, list of aging information 1030 can include data records with open issues that have been in the workflow process for 1-11 days, for 12-22 days for 23-33 days, etc. In many embodiments, a user (e.g., 122-123 (FIG. 1)) can select a day range in list of aging information 1030 to work on data records in that particular aging group or to view information regarding those data records.

In several embodiments, the dashboard in user interface display 1000 can include a list of inbound files 1040. For example, list of inbound files 1040 can show recent source files that have been received as submissions from healthcare entities (e.g., 111-112 (FIG. 1)) and/or responses received from governmental entities (e.g., 131-132 (FIG. 1)). In some embodiments, the most recent inbound file can be included in list of inbound files 1040. In other embodiments, a predetermined or configurable number of the most recent inbound files (e.g., the 20 most recent inbound files) can be included in list of inbound files 1040. In several embodiments, a user (e.g., 122-123 (FIG. 1)) can select an inbound file in list of inbound files 1040 to review data records in the inbound file, and/or to review statistical information regarding the status of the data records in the inbound file, such as to review the number of data records that are open for manual review, the number of records that are ready to be submitted, the number of records that have been submitted to one or more governmental entities (e.g., 131-132 (FIG. 1)), etc.

In several embodiments, the dashboard in user interface display 1000 can include a list of outbound files 1050. For example, list of outbound files 1050 can show recent source files that have been sent to governmental entities (e.g., 131-132 (FIG. 1)). In some embodiments, the most recent outbound file can be included in list of outbound files 1050. In other embodiments, a predetermined or configurable number of the most recent outbound files (e.g., the 20 most recent outbound files) can be included in list of outbound files 1050. In several embodiments, a user (e.g., 122-123 (FIG. 1)) can select an outbound file in list of outbound files 1050 to review data records in the outbound file and/or to review statistical information regarding the status of the data records in the outbound file, such as to review the number of data records that were sent to the governmental entity (e.g., 131-132 (FIG. 1)), the number of data records that were accepted by the governmental entity (e.g., 131-132 (FIG. 1)), the number of data records rejected by the governmental entity (e.g., 131-132 (FIG. 1)), etc.

In many embodiments, the user (e.g., 122-123 (FIG. 1)) can customize the dashboard to select information to view from among list of queues 1010, list of trends 1020, list of aging information 1030, list of inbound files 1040, list of outbound files 1050, and/or other suitable information. In many embodiments, as described above, each individual grouping (e.g., "NPI Issues" queue in list of queues 1010, aging information for day range 1-11 in list of aging information 1030, etc.) can include a link to data records that are defined by that individual grouping.

Turning ahead in the drawings, FIG. 11 illustrates an exemplary user interface display 1100 of the management application, showing a list of data records 1110 defined by an individual grouping in the dashboard of user interface display 1000 (FIG. 10). User interface display 1100 is merely exemplary, and embodiments of the management application can be employed in many different embodiments or examples not specifically depicted or described herein. Management system 121 (FIG. 1) can provide user interface display 1100 to a user (e.g., 122-123 (FIG. 1)) to display and/or manage list of data records 1110 corresponding to an individual grouping in the dashboard of user interface display 1000 (FIG. 10).

For example, the user (e.g., 122-123 (FIG. 1)) can select a queue in list of queues 1010 (FIG. 10) to display list of data records 1110, which can include each of the data records that has been added to the queue for manual processing. In many embodiments, the user (e.g., 122-123 (FIG. 1)) can select a data record from list of data records 1110 in order to manually process that data record.

Turning ahead in the drawings, FIG. 12 illustrates an exemplary user interface display 1200 of the management application, showing a list of queues 1220 for an exemplary transaction type 1210. User interface display 1200 is merely exemplary, and embodiments of the management application can be employed in many different embodiments or examples not specifically depicted or described herein. Management system 121 (FIG. 1) can provide user interface display 1200 to a user (e.g., 122-123 (FIG. 1)) to display and/or manage list of queues 1220 for transaction type 1210.

For example, transaction type 1210 can be institutional encounters, and list of queues 1220 can display queues that can be used for institutional encounters. In various embodiments, user interface display 1200 can be used to add, edit, and/or delete queues in list of queues 1220. For example, a user (e.g., 122-123 (FIG. 1)) can employ user interface display 1200 to create one or more custom queues, such as a queue that includes certain types of review codes. In some embodiments, roles can be assigned to the queues in list of queues 1220 so that certain users or teams of users having a role can work on queues with corresponding roles.

Turning ahead in the drawings, FIG. 13 illustrates an exemplary user interface display 1300 of the management application, showing a list of users 1310 assigned to roles. User interface display 1300 is merely exemplary, and embodiments of the management application can be employed in many different embodiments or examples not specifically depicted or described herein. Management system 121 (FIG. 1) can provide user interface display 1300 to a user (e.g., 122-123 (FIG. 1)) to display and/or manage list of users 1310 and/or roles assigned to the users in list of users 1310.

For example, a user can be assigned to one or more roles, such as the provider team or the eligibility team. Similarly, those roles can be assigned to queues, such that users on the provider team can have access to queues related to the provider team. By separating data records into queues and roles, such as based on review code or error type, management system 121 (FIG. 1) can advantageously facilitate having individual users (e.g., 122-123 (FIG. 1)) with a specialty process data records having certain types of open issues that match that specialty.

Turning ahead in the drawings, FIG. 14 illustrates an exemplary user interface display 1400 of the management application, showing a form for editing an individual data record. User interface display 1400 is merely exemplary, and embodiments of the management application can be employed in many different embodiments or examples not specifically depicted or described herein. Management system 121 (FIG. 1) can provide user interface display 1400 to a user (e.g., 122-123 (FIG. 1)) to review and/or modify a data record.

As shown in FIG. 14, user interface display 1400 can include a data record display 1410, which can include an encounter ID (identifier) field 1411, a status field 1412, and data fields editor 1413. In many embodiments, the encounter ID in encounter ID field 1411 can be a unique identifier for the individual data record. In a number of embodiments, a user (e.g., 122-123 (FIG. 1)) can select how to process the data record, such as to review the encounter, to submit the encounter, the exclude the encounter from submission, or to reject the encounter in status field 1412. In a number of embodiments, when reviewing the data record, a user (e.g., 122-123 (FIG. 1)) can edit one or more of the fields in data fields editor 1413. In many embodiments, data fields editor 1413 can create a user interface based on the data structure (e.g., XML data structure) of the data records, as defined by the data dictionary schema (e.g., in list of data dictionary schema 910 (FIG. 9)) that is associated with the data record. In many embodiments, the user (e.g., 122-123 (FIG. 1)) can manually edit one or more of the data fields in data fields editor 1413 to correct non-compliance issues, such as in a data records that fails one or more steps in the workflow.

In several embodiments, user interface display 1400 can include a list of review codes 1420 that were applied to the data record when the data record was run against the workflow steps (e.g., run against list of steps 220 (FIG. 2) of the workflow to validate the data record). In many embodiments, the review code can include a description to explain the review code. In a number of embodiments, the user (e.g., 122-123 (FIG. 1)) can click on a review code in list of review codes 1420 to determine additional information about why the data record was assigned the review code. In many embodiments, each of the review codes can be displayed in list of review codes 1420, such that a user (e.g., 122-123 (FIG. 1)) that is reviewing the data record can address one or more of the review codes. For example, in some instances, the user (e.g., 122-123 (FIG. 1)) can review each of the review codes and manually correct each of the issues that caused the review codes to be assigned to the data record. Once the review codes have been addressed, the user (e.g., 122-123 (FIG. 1)) can set the data record as ready for submission in status field 1412. In several embodiments, once a data record has been manually updated, the data record can be run against the steps in list of steps 220 (FIG. 2) of the workflow again to validate the data record with the updated data.

Figure 15:
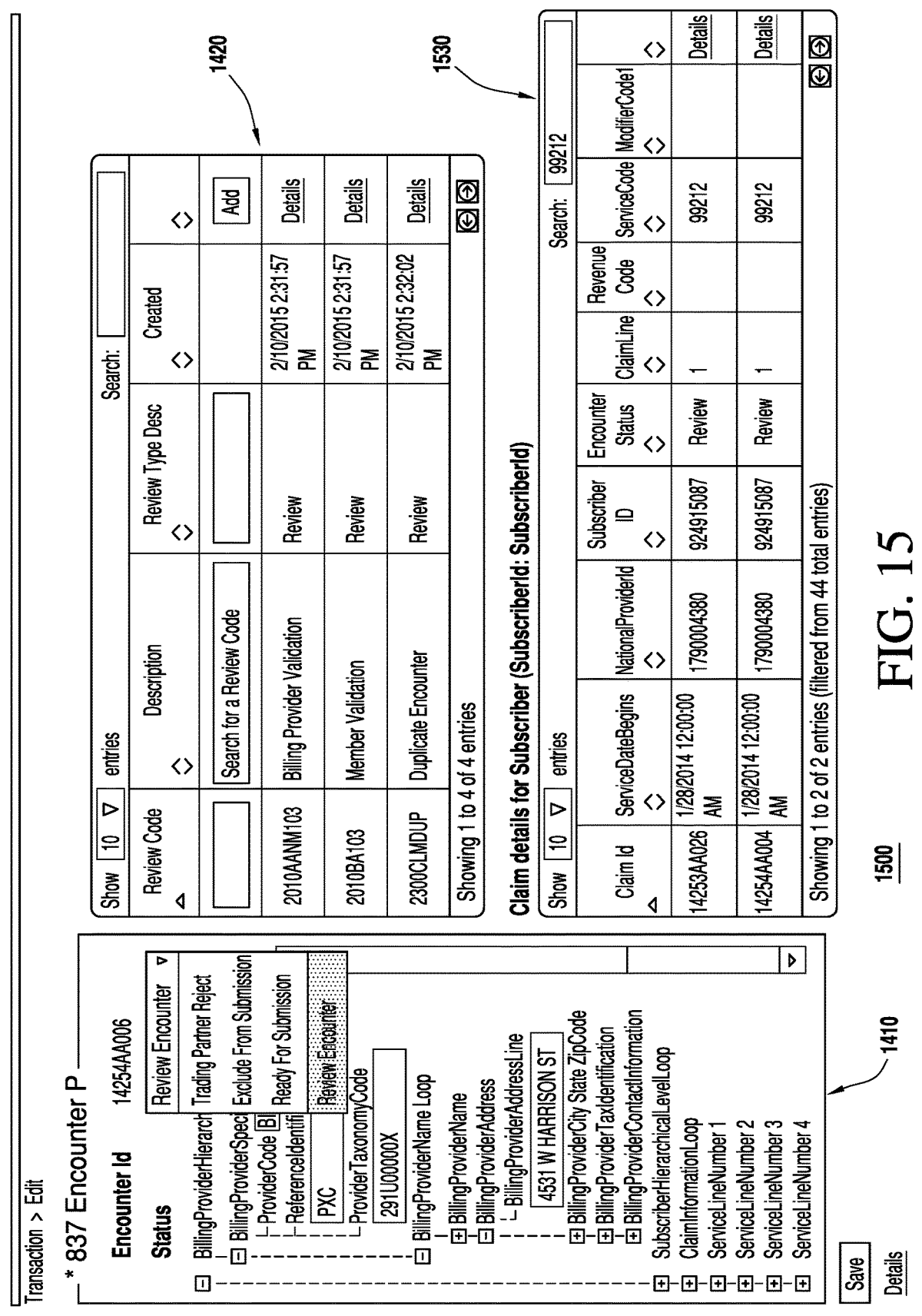

Turning ahead in the drawings, FIG. 15 illustrates an exemplary user interface display 1500 of the management application, showing a form for reviewing an individual data record that has a duplicate entry. User interface display 1500 is merely exemplary, and embodiments of the management application can be employed in many different embodiments or examples not specifically depicted or described herein. Management system 121 (FIG. 1) can provide user interface display 1500 to a user (e.g., 122-123 (FIG. 1)) to determine a duplicate data record.

As shown in FIG. 15, user interface display 1500 can include data record display 1410 and list of review codes 1420. In several embodiments, user interface display 1500 can include one or more other panels, such as claim details for subscriber 1530. In several embodiments, the user interface display (e.g., 1500) provided by management system 121 (FIG. 1) can be customized by the user (e.g., 122-123 (FIG. 1)) to allow the user (e.g., 122-123 (FIG. 1)) to dynamically add or remove various panels of information, such as data record display 1410, list of review codes 1420, claim details for subscriber 1530, etc., which beneficially can allow the user (e.g., 122-123 (FIG. 1)) to create custom views with information that is relevant to the user (e.g., 122-123 (FIG. 1)) when processing the data records. For example, when the user (e.g., 122-123 (FIG. 1)) is reviewing the data record displayed in data record display 1410 and notices that a review code indicates that the data record is a duplicate encounter, the user (e.g., 122-123 (FIG. 1)) can add the panel for claim details for subscriber 1530 to search for records from the subscriber that have the same service code, which can indicate that the subscriber submitted duplicate submissions.

Turning ahead in the drawings, FIG. 16 illustrates an exemplary user interface display 1600 of the management application, showing a list of status codes 1610. User interface display 1600 is merely exemplary, and embodiments of the management application can be employed in many different embodiments or examples not specifically depicted or described herein. Management system 121 (FIG. 1) can provide user interface display 1600 to a user (e.g., 122-123 (FIG. 1)) to review, modify, and/or delete a status code.

As shown in FIG. 16, user interface display 1600 can display list of status codes 1610. In many embodiments, after data records are submitted to a governmental entity (e.g., 131-132 (FIG. 1)), the governmental entity (e.g., 131-132 (FIG. 1)) can send responses back to management application 121 (FIG. 1), which can indicate whether or not the data records submitted to the state were accepted for payment, rejected, or denied payment. If one or more data records are rejected for non-compliance, the responses can includes status codes, such as those status codes included in list of status codes 1610, which can indicate reasons for the rejections by the governmental entity (e.g., 131-132 (FIG. 1)). In several embodiments, the data records having status codes indicating a rejection by the governmental entity (e.g., 131-132 (FIG. 1)) can be added to response queues based on the status code. In various embodiments, existing status codes in list of status codes 1610 can be modified and/or deleted, and/or new status codes can be created through user interface display 1600.

Turning ahead in the drawings, FIG. 17 illustrates an exemplary user interface display 1700 of the management application, showing a list of response queues 1710 corresponding to status codes and a list of data records 1720 that are assigned to one of the response queues in list of response queues 1710. User interface display 1700 is merely exemplary, and embodiments of the management application can be employed in many different embodiments or examples not specifically depicted or described herein. Management system 121 (FIG. 1) can provide user interface display 1700 to a user (e.g., 122-123 (FIG. 1)) to review and/or modify data records in a response queue.

In many embodiments, list of response queues 1710 can include response queues that each correspond to a status code, such as the status codes in list of status codes 1610 (FIG. 16). In many embodiments, each status code in list of response queues 1710 can include the status code corresponding to the response queue, and in some embodiments, can include the number of data records that are assigned to the response queue. For example, list of response queues 1710 can indicate that the response queue for status code "M28" includes 35 data records.

In several embodiments, if a user (e.g., 122-123 (FIG. 1) selects a response queue in list of response queues 1710, user interface display 1700 can display a panel showing list of data records 1720, which can be the data records that are assigned to the response queue due to receiving a rejection from the governmental entity (e.g., 131-132 (FIG. 1)) based on the status code corresponding to the response queue. For example, if the user selects the response queue for the status code M28, which indicates that the encounter submission is missing the admission hour, user interface display 1700 can display list of data records 1720, which includes data records that were rejected with a status code of M28. In various embodiments, the user (e.g., 122-123 (FIG. 1)) can select a data record in list of data records 1720 to address the rejection. For example, the user (e.g., 122-123 (FIG. 1)) can rework the data records in the M28 response queue to correct the issues with the missing admission hour in the data record submissions. In many embodiments, one or more new steps can be added to the workflow, such as described above in FIGS. 3-4, to ensure that the workflow validates data records in the future for the one or more issues that resulted in the rejections from the governmental entity (e.g., 131-132 (FIG. 1)) indicated by the status codes. For example, new steps can be created to ensure the data records include the admission hour before being submitted to the governmental entity (e.g., 131-132 (FIG. 1)).

Turning ahead in the drawings, FIG. 18 illustrates an exemplary user interface display 1800 of the management application, showing a form for reviewing an individual data record and the status codes under which the individual data record was rejected. User interface display 1800 is merely exemplary, and embodiments of the management application can be employed in many different embodiments or examples not specifically depicted or described herein. Management system 121 (FIG. 1) can provide user interface display 1800 to a user (e.g., 122-123 (FIG. 1)) to review and/or modify a data record based on rejections of a data record under one or more status codes.

As shown in FIG. 18, user interface display 1800 can include data record display 1410 and list of review codes 1420. In several embodiments, user interface display 1800 can include one or more other panels, such as a list of status codes 1830. List of status codes 1830 can include each status codes and, in some embodiments, associated details, that explain the rejections of the data record by the governmental entity (e.g., 131-132 (FIG. 1)). For example, list of status codes 1830 can include each of the status codes of the response from the governmental entity (e.g., 131-132 (FIG. 1)) at a line level of the response. In many embodiments, the status code can include a description to explain the status code. In a number of embodiments, the user (e.g., 122-123 (FIG. 1)) can click on a status code in list of status codes 1830 to determine additional details about the status code. In many embodiments, each of the status codes can be displayed in list of status codes 1830, such that a user (e.g., 122-123 (FIG. 1)) that is reviewing the data record can address one or more of the status codes. For example, in some instances, the user (e.g., 122-123 (FIG. 1)) can review each of the status codes and manually correct each of the issues that cause the status codes to be assigned to the data record. Once the status codes have been addressed, the user (e.g., 122-123 (FIG. 1)) can set the data record as ready for resubmission to the governmental entity (e.g., 131-132 (FIG. 1)).

Turning ahead in the drawings, FIG. 19 illustrates an exemplary user interface display 1900 of the management application, showing a form for submitting a file to a governmental entity (e.g., 131-132 (FIG. 1)) for data records that are ready for submission. User interface display 1900 is merely exemplary, and embodiments of the management application can be employed in many different embodiments or examples not specifically depicted or described herein. Management system 121 (FIG. 1) can provide user interface display 1900 to a user (e.g., 122-123 (FIG. 1)) to specify criteria for submission of data records to a governmental entity (e.g., 131-132 (FIG. 1)).

As shown in FIG. 19, user interface display 1900 can include one or more panels to allow a user (e.g., 122-123 (FIG. 1)) to specify criteria for submission of data records to a governmental entity (e.g., 131-132 (FIG. 1)). In a number of embodiments, user interface display 1900 can include a claim form selection panel 1910, a submission type selection panel 1920, a claims IDs selection panel 1930, and/or a batch selection panel 1940. In a number of embodiments, claim form selection panel 1910 can allow a user (e.g., 122-123 (FIG. 1)) to specify the type of claims to be submitted, such as Dental, Institutional, NCPDP (National Council for Prescription Drug Programs), Professional, etc. In several embodiments, submission type selection panel 1920 can allow a user (e.g., 122-123 (FIG. 1)) to select whether the submission is a test submission or an actual production submission. In several embodiments, claims IDs selection panel 1930 can allow a user (e.g., 122-123 (FIG. 1)) to specify the data records to be submitted. For example, the user can choose to send all data records in a ready status that meet the other criteria, or choose to send a subset, such as by entering a list of claim IDs or ranges of claims. In various embodiments, batch selection panel 1940 can allow a user (e.g., 122-123 (FIG. 1)) to choose the trading format for the submission, the batch size of the submission, and/or the claim type of the submission, after which the user (e.g., 122-123 (FIG. 1)) can submit the file to that includes the data records to the governmental entity (e.g., 131-132 (FIG. 1)).

In some embodiments, the file can be created by converting the structured data records (e.g., in XML format) to the flat file format required by the governmental entity (e.g., 131-132 (FIG. 1)), such as X12 837 format. In a number of embodiments, the file can be created and/or submitted in the background after the user has selected the options for submission in user interface display 1900.

Turning ahead in the drawings, FIG. 20 illustrates an exemplary user interface display 2000 of the management application, showing a form for creating transactions for submission to a governmental entity (e.g., 131-132 (FIG. 1)) in different format. User interface display 2000 is merely exemplary, and embodiments of the management application can be employed in many different embodiments or examples not specifically depicted or described herein. Management system 121 (FIG. 1) can provide user interface display 2000 to a user (e.g., 122-123 (FIG. 1)) to specify criteria for submission of data records to a governmental entity (e.g., 131-132 (FIG. 1)) in a different format.

As shown in FIG. 20, user interface display 2000 can include one or more panels to allow a user (e.g., 122-123 (FIG. 1)) to specify criteria for submission of data records to a governmental entity (e.g., 131-132 (FIG. 1)) in a different format. In a number of embodiments, user interface display 2000 can include a claims IDs selection panel 2010 and/or a format selection panel 2020. In several embodiments, claims IDs selection panel 2010 can be similar or identical to claims IDs selection panel 1930 (FIG. 19), and can allow a user (e.g., 122-123 (FIG. 1)) to specify the data records to be submitted. In various embodiments, format selection panel 2020 can allow a user (e.g., 122-123 (FIG. 1)) to choose the format type for the submission to the governmental entity (e.g., 131-132 (FIG. 1)), which can be different than the format type of the data record in the inbound source. For example, a source can include data records in a 837I format for CMS, and the claims in the data records can need to be submitted to more than one governmental entity (e.g., 131-132 (FIG. 1)), such as to both CMS, which requires the 837I format, and to the New York State Department of Health, which requires the MEDS III Institutional format. The claim can be submitted twice as two separate data records, once in each format. The user (e.g., 122-123 (FIG. 1)) can select the appropriate format for the claim submission in format selection panel 2020, such as MEDS III Institutional.

In many embodiments, by validating encounter submissions prior to submission to the governmental entities (e.g., 131-132 (FIG. 1)), management system 121 (FIG. 1) advantageously can generate compliant encounter transactions and greatly reduce the likelihood of receiving rejected encounter transactions. In several embodiments, management system 121 (FIG. 1) beneficially can manage the responses returned from the governmental entities (e.g., 131-132 (FIG. 1)) to update the status of the associated encounter, identify errors with explanations for correction, and facilitate correction and resubmission of the encounters. In various embodiments, management system 121 (FIG. 1) advantageously can identify errors prior to submission and auto-correct the errors where possible, or route the submissions appropriately for manual correction. In a number of embodiments, management system 121 (FIG. 1) beneficially can connect the submissions to responses to allow for readily accessing previously submitted claims for audits and/or other research. In several embodiments, management system 121 advantageously can allow encounter submissions to be processed more quickly in a scalable manner with fewer errors.

In some embodiments, management system 121 (FIG. 1) advantageously can put data where it is needed for manual correction by managing the data by priority and/or exception, and/or placing the data in work queues that can be routed to the appropriate user (e.g., 122-123 (FIG. 1)) for processing and disposition. In various embodiments, management system 121 (FIG. 1) beneficially can coordinate tasks and synchronize data between work groups and system components, and/or can provide access to configurable queues for information when it is needed by the users (e.g., 122-123 (FIG. 1)). In several embodiments, management system 121 (FIG. 1) advantageously can offer an alternative to the costly and time-consuming "rip and replace" procedures associated with upgrading conventional workflow solutions. In a number of embodiments, management system 121 (FIG. 1) beneficially can take data at its source, process it using data dictionary schema and a workflow that is defined by the transaction, and put it back, unlike conventional systems that use a fixed data architectures that replicate and manage the data in rigid workflows. In many embodiments, management system 121 (FIG. 1) advantageously can log the steps performed by the workflow and the updates to the data to create an audit trail for the data records. In several embodiments, management system 121 beneficially can allow process data records more quickly and in a scalable manner with fewer errors.

Figure 21:
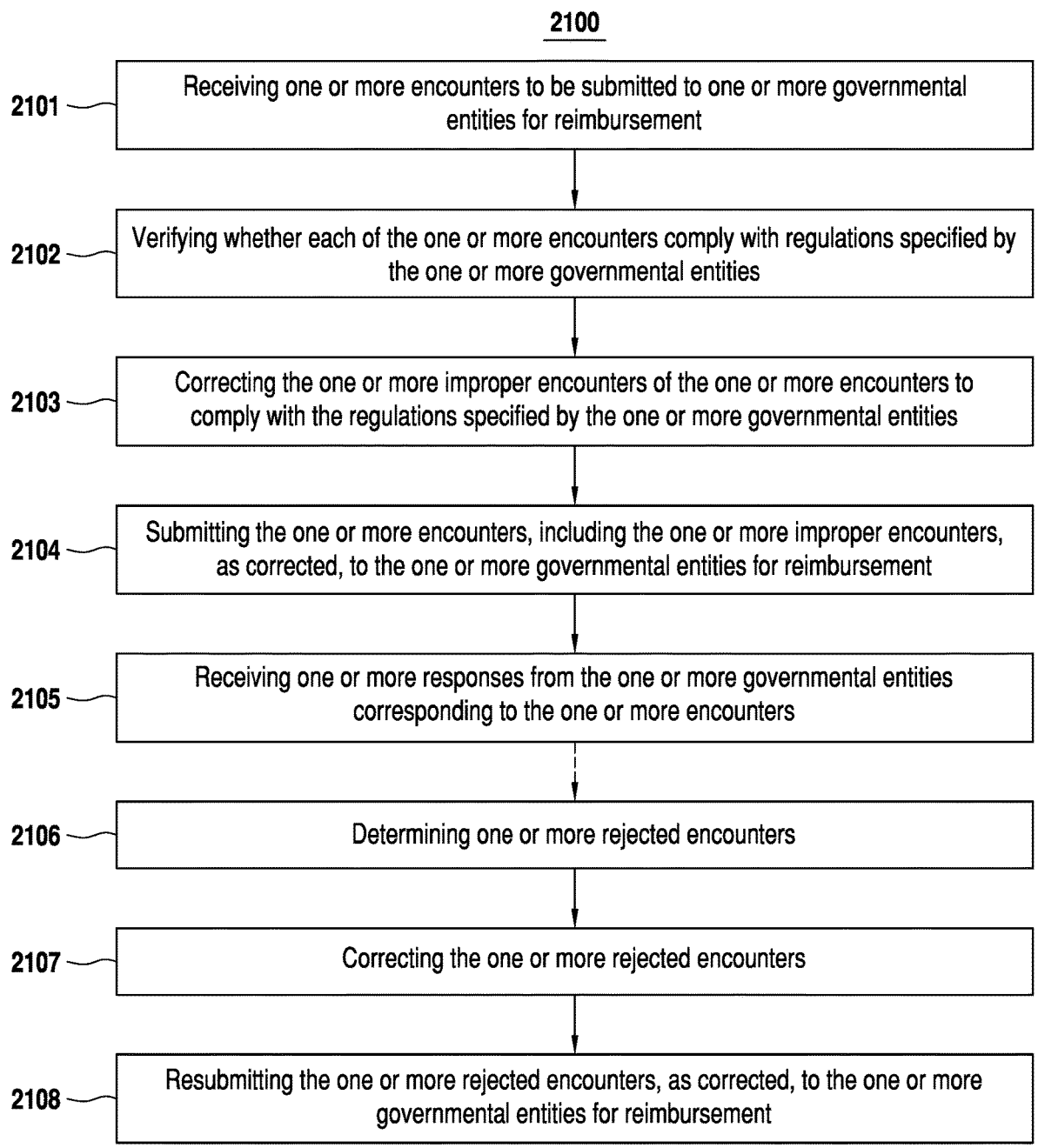
FIG. 21 illustrates a flow chart for an exemplary method of encounter management, according to an embodiment.

Turning ahead in the drawings, FIG. 21 illustrates a flow chart for a method 2100 of encounter management, according to an embodiment. Method 2100 is merely exemplary and is not limited to the embodiments presented herein. Method 2100 can be employed in many different embodiments or examples not specifically depicted or described herein. In some embodiments, the procedures, the processes, and/or the activities of method 2100 can be performed in the order presented. In other embodiments, the procedures, the processes, and/or the activities of method 2100 can be performed in any suitable order. In still other embodiments, one or more of the procedures, the processes, and/or the activities of method 2100 can be combined or skipped.

Referring to FIG. 21, method 2100 can include a block 2101 of receiving one or more encounters to be submitted to one or more governmental entities for reimbursement after the encounters have been adjudicated and paid by a health insurance plan. In some embodiments, the governmental entities can be similar or identical to governmental entities 131-132 (FIG. 1), and/or can include at least one of CMS or one or more State-based Medicaid entities. In a number of embodiments, the encounters can each be transacted in a data record. In several embodiments, the encounters can be received by management system 121 (FIG. 1), such as from a healthcare entity (e.g., 111-112 (FIG. 1)). In many embodiments, the healthcare entity (e.g., 111-112 (FIG. 1)) can be the health insurance plan. In various embodiments, the health insurance plan can adjudicate and pay claims to healthcare providers, then seek reimbursement for the encounters. In many embodiments, each of the one or more encounters can represent a claim for reimbursement for a medical encounter, such as a medical encounter at a healthcare provider. In several embodiments, the one or more encounters can be submitted in at least one of an EDI 837 format or a MEDS III format.

In many embodiments, method 2100 additionally can include a block 2102 of verifying whether each of the one or more encounters comply with regulations specified by the one or more governmental entities to determine one or more improper encounters of the one or more encounters comprising one or more errors that do not comply with the regulations specified by the one or more governmental entities. In some embodiments, management system 121 (FIG. 1) can be process the encounters as data records in a workflow of steps that determine encounters having errors that fail to comply with the regulations of the governmental entities. For example, management system 121 (FIG. 1) can process the encounters through a list of steps of a workflow, such as list of steps 220 (FIG. 2). In many embodiments, the improper encounters can be the encounters that fail one or more of the steps with a review code or that are determined by the one or more steps to require correct, such as automatic correction or manual correction. For example, an improper encounter can be similar or identical to the data record in data record display 1410 (FIGS. 14-15) with the review codes listed in list of review codes 1420 (FIGS. 14-15).

Figure 22:
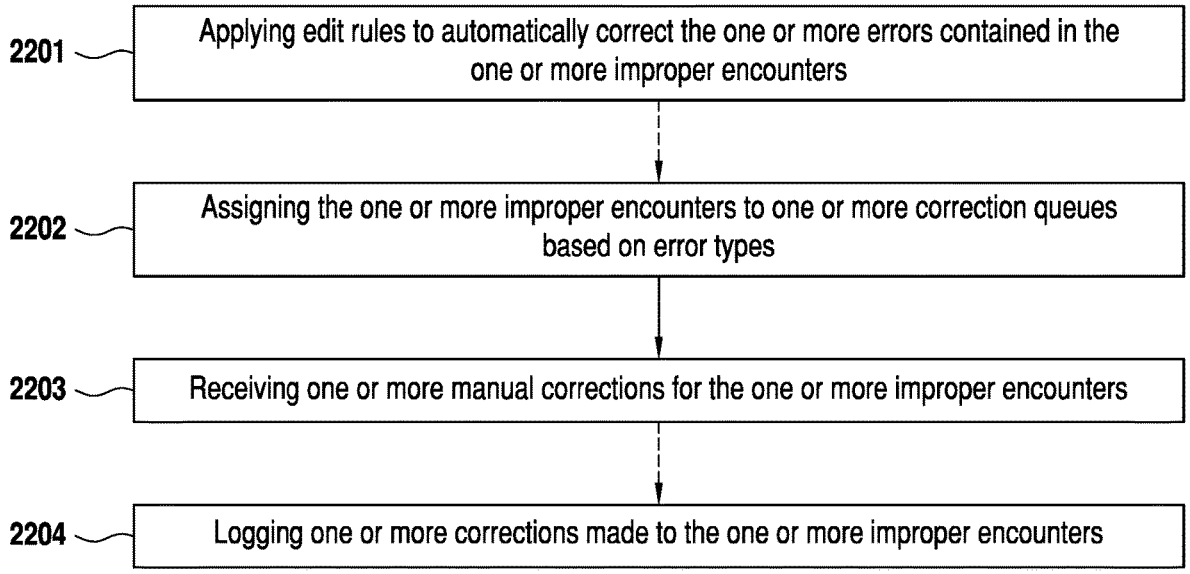
FIG. 22 illustrates a flow chart for an exemplary procedure of correcting the one or more improper encounters of the one or more encounters to comply with the regulations specified by the one or more governmental entities, according to the embodiment of FIG. 21.

In several embodiments, method 2100 further can include a block 2103 of correcting the one or more improper encounters of the one or more encounters to comply with the regulations specified by the one or more governmental entities. For example, in a number of embodiments, management system 121 (FIG. 1) can correct the improper encounters automatically through the application of update rules, such as shown in FIGS. 4-5, and/or manually through correction by one or more users (e.g., 122-123 (FIG. 1)). In some embodiments, block 2103 can be implemented as shown in FIG. 22 and described below.

In many embodiments, method 2100 additionally can include a block 2104 of submitting the one or more encounters, including the one or more improper encounters, as corrected, to the one or more governmental entities for reimbursement. For example, in some embodiments, management system 121 (FIG. 1) can submit files that contain encounter to the governmental entities based on criteria specified by the users (e.g., 122-123 (FIG. 1)), such as shown in FIGS. 19-20. In many embodiments, the files can be sent from management system 121 (FIG. 1) to the governmental entities through network 140 (FIG. 1).

In several embodiments, method 2100 further can include a block 2105 of receiving one or more responses from the one or more governmental entities corresponding to the one or more encounters. For example, management system 121 (FIG. 1) can receive responses from the governmental entities through network 140 (FIG. 1) in response to the submissions set to the governmental entities in block 2104.

In many embodiments, method 2100 optionally can include a block 2106 of determining, based on the one or more responses received from the one or more governmental entities, one or more rejected encounters of the one or more encounters that are rejected by the one or more governmental entities. In some embodiments, each of the rejected encounters can correspond to one or more rejection statuses of the one or more responses. The one or more rejection statuses can be similar or identical to the status codes in list of status codes 1830. In a number of embodiments, management system 121 (FIG. 1) can be process the responses to determine the one or more rejected encounters and match up the responses to the rejected encounters, such as shown in FIG. 18.

Figure 23:
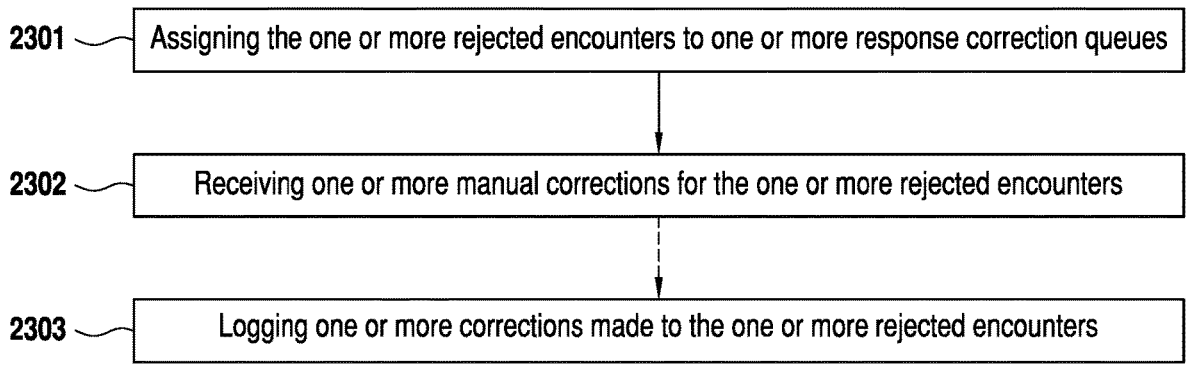
FIG. 23 illustrates a flow chart for an exemplary procedure of correcting the one or more rejected encounters of the one or more encounters based on the one or more rejection statuses, according to the embodiment of FIG. 21.

In several embodiments, method 2100 additionally can include a block 2107 of correcting the one or more rejected encounters of the one or more encounters based on the one or more rejection statuses. For example, in a number of embodiments, management system 121 (FIG. 1) can correct the improper encounters manually through correction by one or more users (e.g., 122-123 (FIG. 1)), such as shown through user interface display 1800, as shown in FIG. 18 and described above. In some embodiments, block 2107 can be implemented as shown in FIG. 23 and described below.

In many embodiments, method 2100 additionally can include a block 2108 of resubmitting the one or more rejected encounters, as corrected, to the one or more governmental entities for reimbursement. For example, in a number of embodiments, management system 121 (FIG. 1) can submit files that contain one or more rejected encounters to the governmental entities based on criteria specified by the users (e.g., 122-123 (FIG. 1)), such as shown in FIGS. 19-20. In many embodiments, the files can be sent from management system 121 (FIG. 1) to the governmental entities through network 140 (FIG. 1).

In a number of embodiments, method 2100 optionally can include providing an XML editor configured to allow manual corrections to the one or more encounters. For example, in a number of embodiments, management system 121 (FIG. 1) can provide an XML editor, such as shown in data fields editor 1413 (FIG. 14), such can be used by a user (e.g., 122-123 (FIG. 1)) to manually correct encounters. For example, a user can manually correct the improper encounters, such as shown in FIGS. 14-15, and/or the rejected encounters, such as shown in FIG. 18.

Turning ahead in the drawings, FIG. 22 illustrates a flow chart for block 2103 of correcting the one or more improper encounters of the one or more encounters to comply with the regulations specified by the one or more governmental entities, according to an embodiment. Block 2103 is merely exemplary and is not limited to the embodiments presented herein. Block 2103 can be employed in many different embodiments or examples not specifically depicted or described herein. In some embodiments, the procedures, the processes, and/or the activities of block 2103 can be performed in the order presented. In other embodiments, the procedures, the processes, and/or the activities of block 2103 can be performed in any suitable order. In still other embodiments, one or more of the procedures, the processes, and/or the activities of block 2103 can be combined or skipped.

Referring to FIG. 22, block 2103 can include a block 2201 of applying edit rules to automatically correct the one or more errors contained in the one or more improper encounters of the one or more encounters. The edit rules can be similar or identical to the update rules, such as the "Billing—PRV Add" update rule shown in FIGS. 4-5 and described above, and/or an assembly, such as the assembly shown in assembly 314 (FIG. 3). In a number of embodiments, an update rule can be combined with a filter rule, such as shown in FIGS. 6 and 8, and described above. For example, management system 121 (FIG. 1) can apply an edit rule to automatically correct one or more errors contained in the one or more improper encounters. In many embodiments, errors that are automatically corrected do not need to be manually corrected.

In many embodiments, block 2103 optionally can include a block 2202 of assigning the one or more improper encounters to one or more correction queues based on error types of the one or more errors contained in the one or more improper encounters. The correction queues can be similar or identical to the queues in list of queues 1220 (FIG. 12). The error types can be similar or identical to the review codes, such as the review codes listed in list of review codes 1420 (FIGS. 14-15, 18). For example, management system 121 (FIG. 1) can assign the one or more improper encounters that have review codes to one or more correction queues based on the review codes.

In several embodiments, block 2103 further can include a block 2203 of receiving one or more manual corrections for the one or more improper encounters in the one or more correction queues. For example, management system 121 (FIG. 1) can receive manual corrections from one or more users (e.g., 122-123 (FIG. 1)) in data fields editor 1413 (FIG. 14).

In many embodiments, block 2103 optionally can include a block 2204 of logging one or more corrections made to the one or more improper encounters. The corrections can be the manual corrections received in block 2203 and/or the automatic corrections made in block 2201. For example, management system 121 (FIG. 1) can create an audit record of any changes made to the encounters within management system 121 (FIG. 1).

Proceeding to the next drawing, FIG. 23 illustrates a flow chart for block 2107 of correcting the one or more rejected encounters of the one or more encounters based on the one or more rejection statuses, according to an embodiment. Block 2107 is merely exemplary and is not limited to the embodiments presented herein. Block 2107 can be employed in many different embodiments or examples not specifically depicted or described herein. In some embodiments, the procedures, the processes, and/or the activities of block 2107 can be performed in the order presented. In other embodiments, the procedures, the processes, and/or the activities of block 2107 can be performed in any suitable order. In still other embodiments, one or more of the procedures, the processes, and/or the activities of block 2107 can be combined or skipped.

Referring to FIG. 23, block 2107 can include a block 2301 of assigning the one or more rejected encounters to one or more response correction queues based on the one or more rejection statuses. The response correction queues can be similar or identical to the response queues in list of response queues 1710 (FIG. 17). In many embodiments, the response queues can be based on the one or more rejection status, such as the one or more status codes. For example, management system 121 (FIG. 1) can assign the one or more rejected encounters that have status codes as rejection statuses to one or more response correction queues based on the rejection statuses.

In several embodiments, block 2107 further can include a block 2302 of receiving one or more manual corrections for the one or more rejected encounters in the one or more response correction queues. For example, management system 121 (FIG. 1) can receive manual corrections from one or more users (e.g., 122-123 (FIG. 1)) in data fields editor 1413 (FIG. 14), and can be corrected such as shown in FIG. 18 and described above.

In many embodiments, block 2107 optionally can include a block 2303 of logging one or more corrections made to the one or more rejected encounters. In some embodiments, the corrections can be the manual corrections received in block 2302. For example, management system 121 (FIG. 1) can create an audit record of any changes made to the encounters within management system 121 (FIG. 1) during processing of the rejected encounters.

Figure 24:
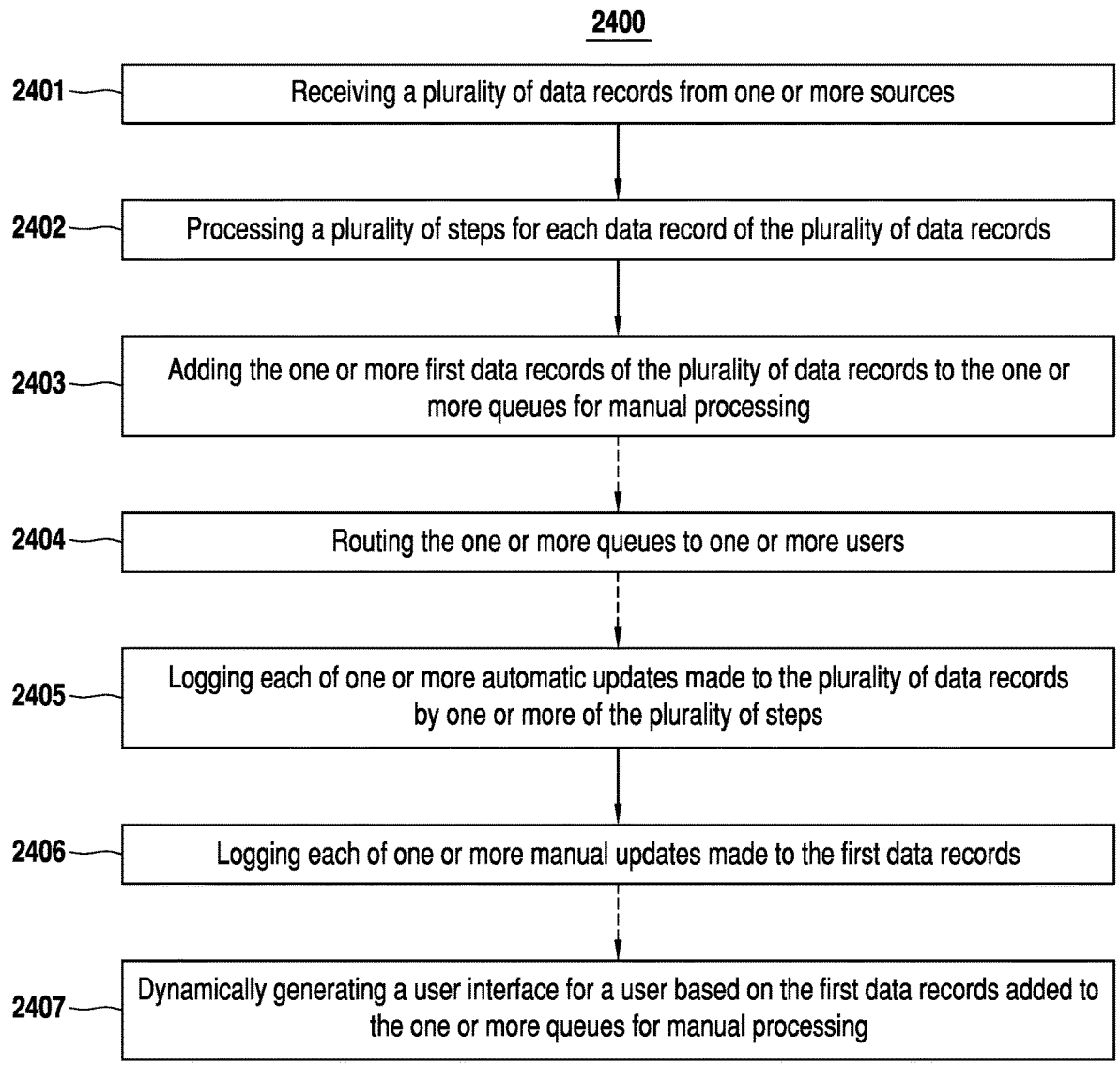
FIG. 24 illustrates a flow chart for an exemplary method of workflow management, according to an embodiment.

Turning ahead in the drawings, FIG. 24 illustrates a flow chart for a method 2400 of workflow management, according to an embodiment. Method 2400 is merely exemplary and is not limited to the embodiments presented herein. Method 2400 can be employed in many different embodiments or examples not specifically depicted or described herein. In some embodiments, the procedures, the processes, and/or the activities of method 2400 can be performed in the order presented. In other embodiments, the procedures, the processes, and/or the activities of method 2400 can be performed in any suitable order. In still other embodiments, one or more of the procedures, the processes, and/or the activities of method 2400 can be combined or skipped.

Referring to FIG. 24, method 2400 can include a block 2401 of receiving a plurality of data records from one or more sources. The sources can be similar or identical to source 210 (FIG. 2) of data records, which can be sent from one or more entities, such as healthcare entities (e.g., 111-112 (FIG. 1)). In a number of embodiments, each data record of the plurality of data records can include a data format. For example, the data format can be similar or identical to a format required by a receiving entity, such as governmental entities 131-132 (FIG. 1). In some embodiments, the data format of at least one of the plurality of data records can be the EDI 837 format. In several embodiments, each data record of the plurality of data records can include a transaction type. For example, the transaction type can be the type of transaction of the data record, such as a State of Illinois Institutional Encounter submission. In some embodiments, the transaction type of at least one of the plurality of data records can be a CMS reimbursement claim.

In many embodiments, method 2400 additionally can include a block 2402 of processing a plurality of steps for each data record of the plurality of data records. In many embodiments, the plurality of steps can be similar or identical to the steps in list of steps 220 (FIG. 2) of the workflow shown in FIG. 2. In many embodiments, the plurality of steps processed for each data record of the plurality of data records can differ depending on the transaction type of the data record. For example, different steps can be performed for different transaction types, such that the workflow can be based upon the transaction type.

In a number of embodiments, one or more of the plurality of steps can interface with each data record of the plurality of data records based on a data dictionary schema corresponding to the data format of the data record. The data dictionary schema can be similar or identical to the data dictionary schema in list of data dictionary schema 910 (FIG. 9). For example, the steps can be defined to interact with the structure of the data records based on the data dictionary schema. In various embodiments, the plurality of data records from the one or more sources can be converted to an XML format, before processing the plurality of steps in block 2402, based on the data dictionary schema corresponding to the data format of each data record of the plurality of data records In a number of embodiments, one or more first steps of the plurality of steps can be configured to conditionally add one or more first data records of the plurality of data records to one or more queues for manual processing. The queues can be similar or identical to the queues in list of queues 1220 (FIG. 12). For example, management system 121 (FIG. 1) can assign the one or more first data records to one or more queues based on the data records satisfying one or more conditions, such as exception conditions (e.g., failing one or more steps in the plurality of steps).

In several embodiments, method 2400 further can include a block 2403 of adding the one or more first data records of the plurality of data records to the one or more queues for manual processing. In a number of embodiments, each of the one or more first data records of the plurality of data records can be added to one or more of the one or more queues based on one or more exception conditions being satisfied in one or more of the one or more first steps of the plurality of steps. For example, management system 121 (FIG. 1) can add a data record to a queue based on the data record failing a step when the step is processed for the data record, and, in many embodiments, can add the data record to another queue based on the data record failing a second step when the second step is process for the data record.

In a number of embodiments, the plurality of steps processed for each transaction type can be customizable by a user (e.g., users 122-123 (FIG. 1)). For example, the user can edit the steps in the workflow, such as shown in FIG. 2 and described above, and/or edit the operations performed by the steps, such as shown in FIGS. 3-6 and 8, and described above. In many embodiments, the one or more queues for manual processing can be customizable by a user, such as by the user creating a queue and/or defining a role for a queue, as shown in FIG. 12 and described above, and/or by assigning a step to a queue, such as in queue field 322 (FIGS. 3-4).

In various embodiments, block 2403 of adding the one or more first data records of the plurality of data records to the one or more queues for manual processing can include, for each data record, processing each of the plurality of steps for the data record before the data record is manually processed in the one or more queues. For example, in some embodiments, management system 121 (FIG. 1), can process each of the steps in the plurality of steps of the workflow for a data record to identify each of the exception conditions before the data records is manually processed by a user. In other embodiments, management system 121 (FIG. 1) can process a data record through the steps until there is an exception condition, and stop processing when an exception condition is encountered.

In some embodiments, one or more of the plurality of steps each can include an update rule configured to automatically modify a data record of the plurality of data records. For example, the update rule can be similar or identical to the "Billing—PRV Add" update rule shown in FIGS. 4-5 and described above, and/or an assembly, such as the assembly shown in assembly 314 (FIG. 3), which in some cases can update the data record automatically. For example, management system 121 (FIG. 1) can apply an update rule to automatically generate correct fields in the one or more data records.

In several embodiments, one or more of the plurality of steps each can include a filter rule and an update rule. The filter rule can be similar to the filter rule shown in FIGS. 6 and 8, and described above. In many embodiments, the update rule can be configured to automatically modify a data record of the plurality of data records if the data record satisfies a condition of the filter rule. For example, management system 121 (FIG. 1) can apply an update rule to automatically correct one or more errors contained in the one or more data records that were flagged as exception conditions the filter rule. In many embodiments, errors that are automatically corrected do not need to be manually corrected.

In many embodiments, method 2400 optionally can include a block 2404 of routing the one or more queues to one or more users when the one or more queues contain the one or more first data records of the plurality of data records. For example, when one or more data records have been added to a queue, the queue can be routed, such as assigned, to a user for manual processing. In many embodiments, the queue can be assigned a role and can be assigned to one or more users based on the roles of the users, as described above.

In several embodiments, method 2400 optionally can include a block 2405 of logging each of one or more automatic updates made to the plurality of data records by one or more of the plurality of steps. For example, management system 121 (FIG. 1) can create an audit record of any automatic changes made to the data records within management system 121 (FIG. 1).

In many embodiments, method 2400 additionally can include a block 2406 of logging each of one or more manual updates made to the first data records of the plurality of data records after the first data records are added the one or more queues for manual processing. For example, management system 121 (FIG. 1) can create an audit record of any manual changes made to the data records within management system 121 (FIG. 1).

In several embodiments, method 2400 optionally can include a block 2407 of dynamically generating a user interface for a user based on the first data records of the plurality of data records added to the one or more queues for manual processing. For example, as shown in FIGS. 15 and 18 and described above, management system 121 (FIG. 1) can generate a dynamic user interface, such as user interface display 1500 (FIG. 15) and/or user interface display 1800 (FIG. 18), which can include one or more panels that are dynamically generated based on the data, such as claim details for subscriber 1530 (FIG. 15), list of status codes 1830 (FIG. 18), and/or other panels.

Figure 25:
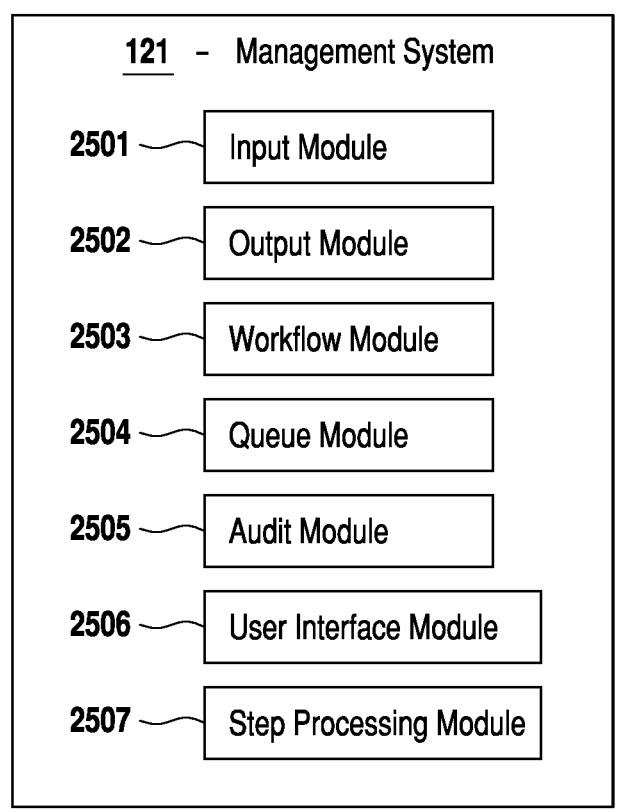
FIG. 25 illustrates a block diagram showing various modules of the management system of FIG. 1.

Turning ahead in the drawings, FIG. 25 illustrates a block diagram of management system 121, according to the embodiment shown in FIG. 1. Management system 121 and the modules therein are merely exemplary and are not limited to the embodiments presented herein. Management system 121 can be employed in many different embodiments or examples not specifically depicted or described herein. In some embodiments, certain elements or modules of Management system 121 can perform various procedures, processes, and/or acts. In other embodiments, the procedures, processes, and/or acts can be performed by other suitable elements or modules.

In some embodiments, management system 121 can include an input module 2501. In certain embodiments, input module 2501 can at least partially perform block 2101 (FIG. 21) of receiving one or more encounters to be submitted to one or more governmental entities for reimbursement after the encounters have been adjudicated and paid by a health insurance plan, block 2105 (FIG. 21) of receiving one or more responses from the one or more governmental entities corresponding to the one or more encounters, and/or block 2401 (FIG. 24) of receiving a plurality of data records from one or more sources.

In many embodiments, management system 121 can include an output module 2502. In certain embodiments, output module 2502 can at least partially perform block 2104 (FIG. 21) of submitting the one or more encounters, including the one or more improper encounters, as corrected, to the one or more governmental entities for reimbursement and/or block 2108 (FIG. 21) of resubmitting the one or more rejected encounters, as corrected, to the one or more governmental entities for reimbursement. In some embodiments, for example, input module 2501 and/or output module 2502 can include Biztalk Server, developed and licensed by Microsoft Corporation of Redmond, Wash., which can handle file transfers from trading partners, and, in a number of embodiments, can include RESTful Services of Visual Studio, also developed and licensed by Microsoft Corporation, which can manage the data records and initiate operations to be performed with the data records, such as to post the data records to initiate a workflow. In other embodiments, different components and/or elements can be used to perform input module 2501 and/or output module 2502.

In a number of embodiments, management system 121 can include a workflow module 2503. In certain embodiments, workflow module 2503 can at least partially perform block 2102 (FIG. 21) of verifying whether each of the one or more encounters comply with regulations specified by the one or more governmental entities to determine one or more improper encounters of the one or more encounters comprising one or more errors that do not comply with the regulations specified by the one or more governmental entities and/or block 2402 (FIG. 24) of processing a plurality of steps for each data record of the plurality of data records.

In several embodiments, management system 121 can include a queue module 2504. In certain embodiments, queue module 2504 can at least partially perform block 2202 (FIG. 22) of assigning the one or more improper encounters to one or more correction queues based on error types of the one or more errors contained in the one or more improper encounters, block 2301 (FIG. 23) of assigning the one or more rejected encounters to one or more response correction queues based on the one or more rejection statuses, block 2403 (FIG. 24) of adding the one or more first data records of the plurality of data records to the one or more queues for manual processing, and/or block 2404 (FIG. 24) of routing the one or more queues to one or more users when the one or more queues contain the one or more first data records of the plurality of data records.

In various embodiments, management system 121 can include an audit module 2505. In certain embodiments, audit module 2505 can at least partially perform block 2204 (FIG. 22) of logging one or more corrections made to the one or more improper encounters, block 2303 (FIG. 23) of logging one or more corrections made to the one or more rejected encounters, block 2405 (FIG. 24) of logging each of one or more automatic updates made to the plurality of data records by one or more of the plurality of steps, and/or block 2406 (FIG. 24) of logging each of one or more manual updates made to the first data records of the plurality of data records after the first data records are added the one or more queues for manual processing In some embodiments, management system 121 can include a user interface module 2506. In certain embodiments, user interface module 2506 can at least partially perform block 2103 (FIG. 21) of correcting the one or more improper encounters of the one or more encounters to comply with the regulations specified by the one or more governmental entities, block 2107 (FIG. 21) of correcting the one or more rejected encounters of the one or more encounters based on the one or more rejection statuses, block 2203 (FIG. 22) of receiving one or more manual corrections for the one or more improper encounters in the one or more correction queues, and/or block 2407 (FIG. 24) of dynamically generating a user interface for a user based on the first data records of the plurality of data records added to the one or more queues for manual processing. In a number of embodiments, user interface module 2506 can present a user interface display, such as user interface display 200 (FIG. 2), user interface display 300 (FIG. 3), user interface display 400 (FIG. 4), user interface display 500 (FIG. 5), user interface display 600 (FIG. 6), user interface display 700 (FIG. 7), user interface display 800 (FIG. 8), user interface display 900 (FIG. 9), user interface display 1000 (FIG. 10), user interface display 1100 (FIG. 11), user interface display 1200 (FIG. 12), user interface display 1300 (FIG. 13), user interface display 1400 (FIG. 14), user interface display 1500 (FIG. 15), user interface display 1600 (FIG. 16), user interface display 1700 (FIG. 17), user interface display 1800 (FIG. 18), user interface display 1900 (FIG. 19), and/or user interface display 2000 (FIG. 20).

In many embodiments, management system 121 can include a step processing module 2507. In certain embodiments, step processing module 2507 can at least partially perform block 2102 (FIG. 21) of verifying whether each of the one or more encounters comply with regulations specified by the one or more governmental entities to determine one or more improper encounters of the one or more encounters comprising one or more errors that do not comply with the regulations specified by the one or more governmental entities, block 2103 (FIG. 21) of correcting the one or more improper encounters of the one or more encounters to comply with the regulations specified by the one or more governmental entities, block 2106 (FIG. 21) of determining, based on the one or more responses received from the one or more governmental entities, one or more rejected encounters of the one or more encounters that are rejected by the one or more governmental entities, block 2107 (FIG. 21) of correcting the one or more rejected encounters of the one or more encounters based on the one or more rejection statuses, block 2201 (FIG. 22) of applying edit rules to automatically correct the one or more errors contained in the one or more improper encounters of the one or more encounters, block 2402 (FIG. 24) of processing a plurality of steps for each data record of the plurality of data records, and/or block 2403 (FIG. 24) of adding the one or more first data records of the plurality of data records to the one or more queues for manual processing.

Figure 26:
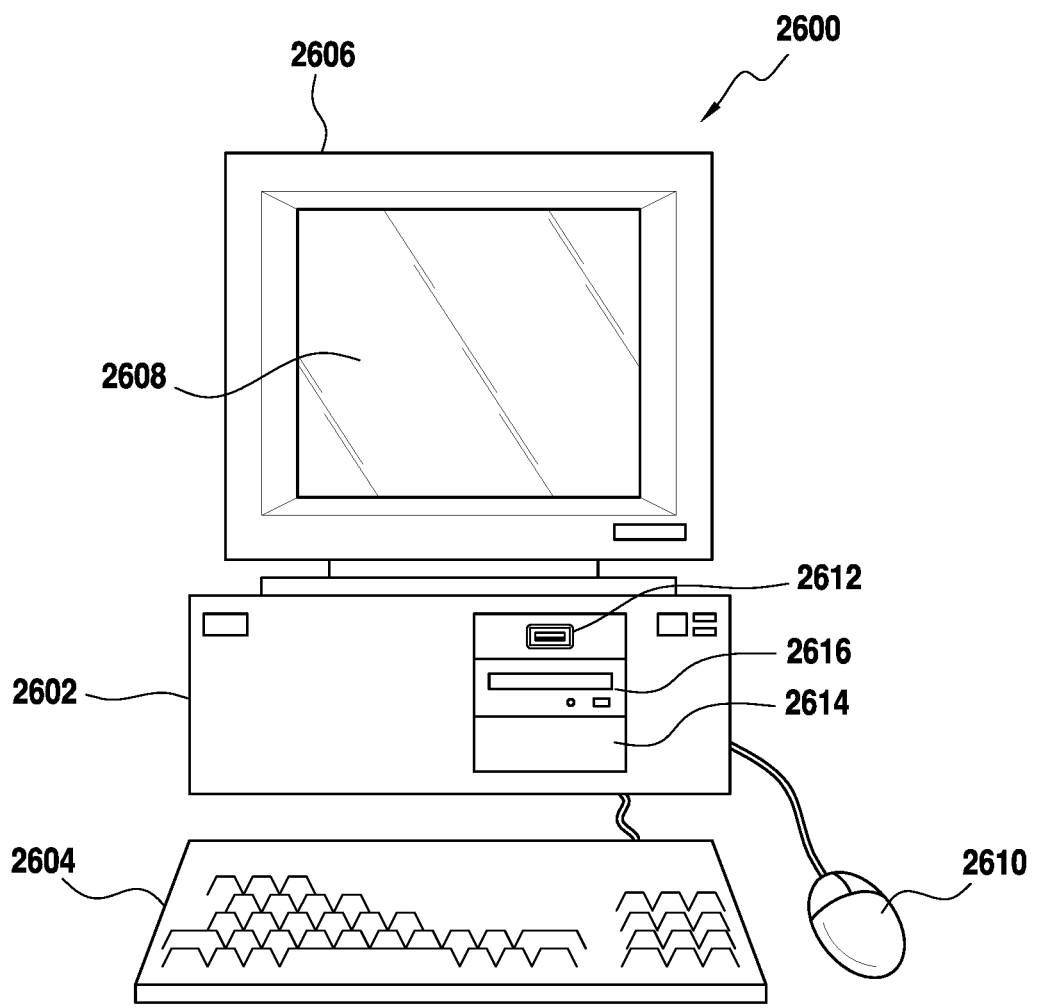
FIG. 26 illustrates a computer that is suitable for implementing an embodiment of the management system of FIG. 1.
Figure 27:
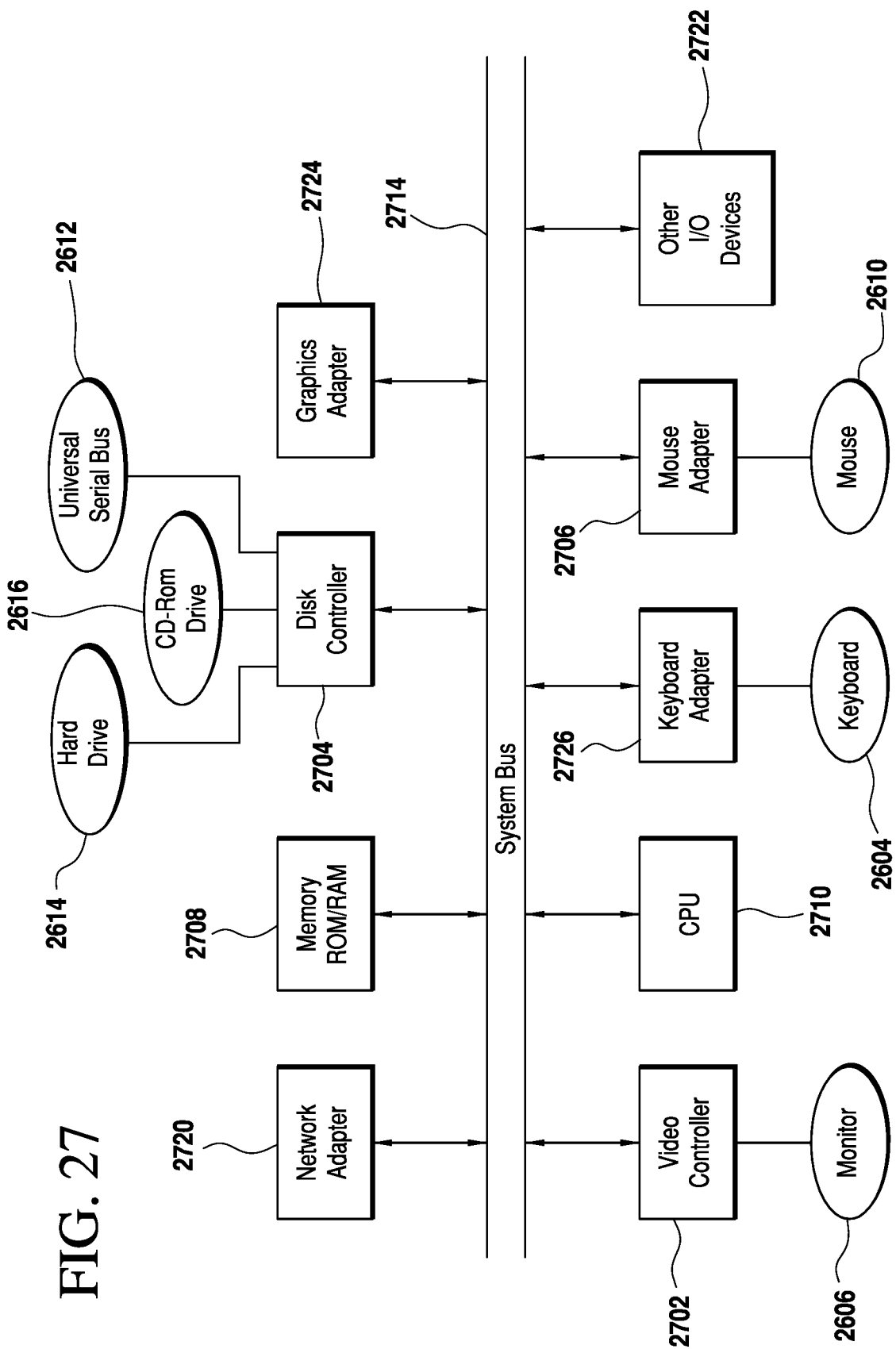
FIG. 27 illustrates a representative block diagram of an example of elements included in circuit boards inside a chassis of the computer of FIG. 26.

Turning ahead in the drawings, FIG. 26 illustrates a computer 2600, all of which or a portion of which can be suitable for implementing an embodiment of or at least a portion of management system 121 (FIGS. 1, 25), and/or the techniques described in method 2100 (FIG. 21), method 2200 (FIG. 22), method 2300 (FIG. 23), and/or method 2400 (FIG. 24). Computer 2600 includes a chassis 2602 containing one or more circuit boards (not shown), a USB (universal serial bus) port 2612, a Compact Disc Read-Only Memory (CD-ROM) and/or Digital Video Disc (DVD) drive 2616, and a hard drive 2614. A representative block diagram of the elements included on the circuit boards inside chassis 2602 is shown in FIG. 27. A central processing unit (CPU) 2710 in FIG. 27 is coupled to a system bus 2714 in FIG. 27. In various embodiments, the architecture of CPU 2710 can be compliant with any of a variety of commercially distributed architecture families.

Continuing with FIG. 27, system bus 2714 also is coupled to memory 2708 that includes both read only memory (ROM) and random access memory (RAM). Non-volatile portions of memory storage unit 2708 or the ROM can be encoded with a boot code sequence suitable for restoring computer 2600 (FIG. 26) to a functional state after a system reset. In addition, memory 2708 can include microcode such as a Basic Input-Output System (BIOS). In some examples, the one or more memory storage units of the various embodiments disclosed herein can comprise memory storage unit 2708, a USB-equipped electronic device, such as, an external memory storage unit (not shown) coupled to universal serial bus (USB) port 2612 (FIGS. 26-27), hard drive 2614 (FIGS. 26-27), and/or CD-ROM or DVD drive 2616 (FIGS. 26-27). In the same or different examples, the one or more memory storage units of the various embodiments disclosed herein can comprise an operating system, which can be a software program that manages the hardware and software resources of a computer and/or a computer network. The operating system can perform basic tasks such as, for example, controlling and allocating memory, prioritizing the processing of instructions, controlling input and output devices, facilitating networking, and managing files. Some examples of common operating systems can comprise Microsoft® Windows® operating system (OS), Mac® OS, UNIX® OS, and Linux® OS.

As used herein, "processor" and/or "processing module" means any type of computational circuit, such as but not limited to a microprocessor, a microcontroller, a controller, a complex instruction set computing (CISC) microprocessor, a reduced instruction set computing (RISC) microprocessor, a very long instruction word (VLIW) microprocessor, a graphics processor, a digital signal processor, or any other type of processor or processing circuit capable of performing the desired functions. In some examples, the one or more processors of the various embodiments disclosed herein can comprise CPU 2710.

In the depicted embodiment of FIG. 27, various I/O devices such as a disk controller 2704, a graphics adapter 2724, a video controller 2702, a keyboard adapter 2726, a mouse adapter 2706, a network adapter 2720, and other I/O devices 2722 can be coupled to system bus 2714. Keyboard adapter 2726 and mouse adapter 2706 are coupled to a keyboard 2604 (FIGS. 26 and 27) and a mouse 2610 (FIGS. 26 and 27), respectively, of computer 2600 (FIG. 26). While graphics adapter 2724 and video controller 2702 are indicated as distinct units in FIG. 27, video controller 2702 can be integrated into graphics adapter 2724, or vice versa in other embodiments. Video controller 2702 is suitable for refreshing a monitor 2606 (FIGS. 26 and 27) to display images on a screen 2608 (FIG. 26) of computer 2600 (FIG. 26). Disk controller 2704 can control hard drive 2614 (FIGS. 26 and 27), USB port 2612 (FIGS. 26 and 27), and CD-ROM or DVD drive 2616 (FIGS. 26 and 27). In other embodiments, distinct units can be used to control each of these devices separately.

In some embodiments, network adapter 2720 can comprise and/or be implemented as a WNIC (wireless network interface controller) card (not shown) plugged or coupled to an expansion port (not shown) in computer system 2600 (FIG. 26). In other embodiments, the WNIC card can be a wireless network card built into computer system 2600 (FIG. 26). A wireless network adapter can be built into computer system 2600 (FIG. 26) by having wireless communication capabilities integrated into the motherboard chipset (not shown), or implemented via one or more dedicated wireless communication chips (not shown), connected through a PCI (peripheral component interconnector) or a PCI express bus of computer system 2600 (FIG. 26) or USB port 2612 (FIG. 26). In other embodiments, network adapter 2720 can comprise and/or be implemented as a wired network interface controller card (not shown).

Although many other components of computer 2600 (FIG. 26) are not shown, such components and their interconnection are well known to those of ordinary skill in the art. Accordingly, further details concerning the construction and composition of computer 2600 and the circuit boards inside chassis 2602 (FIG. 26) need not be discussed herein.

When computer 2600 in FIG. 26 is running, program instructions stored on a USB drive in USB port 2612, on a CD-ROM or DVD in CD-ROM and/or DVD drive 2616, on hard drive 2614, or in memory 2708 (FIG. 27) are executed by CPU 2710 (FIG. 27). A portion of the program instructions, stored on these devices, can be suitable for carrying out all or at least part of the techniques described herein. In various embodiments, computer 2600 can be reprogrammed with one or more modules, applications, and/or databases, such as those described herein, to convert a general purpose computer to a special purpose computer. For purposes of illustration, programs and other executable program components are shown herein as discrete systems, although it is understood that such programs and components may reside at various times in different storage components of computer 2600, and can be executed by CPU 2710. Alternatively, or in addition to, the systems and procedures described herein can be implemented in hardware, or a combination of hardware, software, and/or firmware. For example, one or more application specific integrated circuits (ASICs) can be programmed to carry out one or more of the systems and procedures described herein. For example, one or more of the programs and/or executable program components described herein can be implemented in one or more ASICs.

Although computer 2600 is illustrated as a desktop computer in FIG. 26, there can be examples where computer 2600 may take a different form factor while still having functional elements similar to those described for computer 2600. In some embodiments, computer 2600 may comprise a single computer, a single server, or a cluster or collection of computers or servers, or a cloud of computers or servers. Typically, a cluster or collection of servers can be used when the demand on computer 2600 exceeds the reasonable capability of a single server or computer. In certain embodiments, computer 2600 may comprise a portable computer, such as a laptop computer. In certain other embodiments, computer 2600 may comprise a mobile device, such as a smartphone. In certain additional embodiments, computer 2600 may comprise an embedded system.

Although encounter management and workflow management have been described with reference to specific embodiments, it will be understood by those skilled in the art that various changes may be made without departing from the spirit or scope of the disclosure. Accordingly, the disclosure of embodiments is intended to be illustrative of the scope of the disclosure and is not intended to be limiting. It is intended that the scope of the disclosure shall be limited only to the extent required by the appended claims. For example, to one of ordinary skill in the art, it will be readily apparent that any element of FIGS. 1-27 may be modified, and that the foregoing discussion of certain of these embodiments does not necessarily represent a complete description of all possible embodiments. For example, one or more of the procedures, processes, or activities of FIGS. 21-24 may include different procedures, processes, and/or activities and be performed by many different modules, in many different orders, and/or one or more of the procedures, processes, or activities of FIGS. 21-24 may include one or more of the procedures, processes, or activities of another different one of FIGS. 21-24.

Replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A system for encounter management, the system comprising:
   one or more processors; and
   one or more non-transitory computer-readable media storing computing instructions configured to run on the one or more processors and perform:
      providing a user interface, the user interface comprising multiple selectable displays comprising:

a first display of the multiple selectable displays configured to receive one or more modifications to a selection of steps in one or more workflows;
a second display of the multiple selectable displays configured to receive one or more modifications to one or more of the steps in the one or more workflows by identifying one or more data rules executed at the one or more of the steps; and
a third display of the multiple selectable displays configured to receive specifications for the one or more data rules;
receiving one or more encounters to be submitted to one or more governmental entities after the one or more encounters have been adjudicated and paid by a health insurance plan;
converting data records of the one or more encounters into XML records using a first data dictionary schema corresponding to a data format of the data records of the one or more encounters;
verifying whether each of the one or more encounters comply with regulations specified by the one or more governmental entities to determine one or more improper encounters of the one or more encounters comprising one or more errors that do not comply with the regulations specified by the one or more governmental entities, comprising:
processing the XML records by applying an applicable workflow of steps based on different sets of rules for different encounter submission types using the first data dictionary schema across the different encounter submission types;
correcting the one or more improper encounters of the one or more encounters to comply with the regulations specified by the one or more governmental entities, comprising:
applying combination filter-and-update rules to first records of the XML records;
adding second records of the XML records to multiple different queues for manual processing; and
dynamically generating different user interface displays for different users handling manual processing of the multiple different queues, the different user interface displays comprising multiple panels, a panel of the multiple panels comprising a list of review codes that differs across the different user interface displays based on differences in data in the second records being manually processed, and each of the different user interface displays being customizable by the different users to add additional panels or remove one or more of the multiple panels;
submitting the one or more encounters, including the one or more improper encounters, as corrected, in an EDI 837 format to the one or more governmental entities; and
receiving one or more responses from the one or more governmental entities corresponding to the one or more encounters.

2. The system of claim 1, wherein correcting the one or more improper encounters of the one or more encounters to comply with the regulations specified by the one or more governmental entities comprises:
applying edit rules to automatically correct the one or more errors contained in the one or more improper encounters of the one or more encounters.

3. The system of claim 1, wherein correcting the one or more improper encounters of the one or more encounters to comply with the regulations specified by the one or more governmental entities comprises:
assigning the one or more improper encounters to one or more correction queues based on error types of the one or more errors contained in the one or more improper encounters; and
receiving one or more manual corrections for the one or more improper encounters in the one or more correction queues.

4. The system of claim 1, wherein correcting the one or more improper encounters of the one or more encounters to comply with the regulations specified by the one or more governmental entities comprises:
logging one or more corrections made to the one or more improper encounters.

5. The system of claim 1, wherein the computing instructions are further configured to perform:
determining, based on the one or more responses received from the one or more governmental entities, one or more rejected encounters of the one or more encounters that are rejected by the one or more governmental entities, wherein each of the one or more rejected encounters corresponds to one or more rejection statuses of the one or more responses;
correcting the one or more rejected encounters of the one or more encounters based on the one or more rejection statuses; and
resubmitting the one or more rejected encounters, as corrected, to the one or more governmental entities.

6. The system of claim 5, wherein correcting the one or more rejected encounters of the one or more encounters based on the one or more rejection statuses comprises:
assigning the one or more rejected encounters to one or more response correction queues based on the one or more rejection statuses; and
receiving one or more manual corrections for the one or more rejected encounters in the one or more response correction queues.

7. The system of claim 5, wherein correcting the one or more rejected encounters of the one or more encounters based on the one or more rejection statuses comprises:
logging one or more corrections made to the one or more rejected encounters.

8. The system of claim 1, wherein the one or more governmental entities comprise at least one of CMS or one or more State-based Medicaid entities.

9. The system of claim 1, wherein the one or more encounters are submitted to multiple different governmental entities.

10. The system of claim 1, wherein the computing instructions are further configured to perform:
integrating with each of the different user interface displays an XML editor configured to allow manual corrections to the one or more encounters.

11. A method for encounter management, the method being implemented via execution of computer instructions configured to run at one or more processors and configured to be stored at one or more non-transitory computer-readable media, the method comprising:
providing a user interface, the user interface comprising multiple selectable displays comprising:
a first display of the multiple selectable displays configured to receive one or more modifications to a selection of steps in one or more workflows;
a second display of the multiple selectable displays configured to receive one or more modifications to one or more of the steps in the one or more workflows by identifying one or more data rules executed at the one or more of the steps; and a third display of the multiple selectable displays configured to receive specifications for the one or more data rules;

receiving one or more encounters to be submitted to one or more governmental entities after the one or more encounters have been adjudicated and paid by a health insurance plan;

converting data records of the one or more encounters into XML records using a first data dictionary schema corresponding to a data format of the data records of the one or more encounters;

verifying whether each of the one or more encounters comply with regulations specified by the one or more governmental entities to determine one or more improper encounters of the one or more encounters comprising one or more errors that do not comply with the regulations specified by the one or more governmental entities, comprising:

processing the XML records by applying an applicable workflow of steps based on different sets of rules for different encounter submission types using the first data dictionary schema across the different encounter submission types;

correcting the one or more improper encounters of the one or more encounters to comply with the regulations specified by the one or more governmental entities, comprising:

applying combination filter-and-update rules to first records of the XML records;

adding second records of the XML records to multiple different queues for manual processing; and dynamically generating different user interface displays for different users handling manual processing of the multiple different queues, the different user interface displays comprising multiple panels, a panel of the multiple panels comprising a list of review codes that differs across the different user interface displays based on differences in data in the second records being manually processed, and each of the different user interface displays being customizable by the different users to add additional panels or remove one or more of the multiple panels;

submitting the one or more encounters, including the one or more improper encounters, as corrected, in an EDI 837 format to the one or more governmental entities; and receiving one or more responses from the one or more governmental entities corresponding to the one or more encounters.

12. The method of claim 11, wherein correcting the one or more improper encounters of the one or more encounters to comply with the regulations specified by the one or more governmental entities comprises:

applying edit rules to automatically correct the one or more errors contained in the one or more improper encounters of the one or more encounters.

13. The method of claim 11, wherein correcting the one or more improper encounters of the one or more encounters to comply with the regulations specified by the one or more governmental entities comprises:

assigning the one or more improper encounters to one or more correction queues based on error types of the one or more errors contained in the one or more improper encounters; and receiving one or more manual corrections for the one or more improper encounters in the one or more correction queues.

14. The method of claim 11, wherein correcting the one or more improper encounters of the one or more encounters to comply with the regulations specified by the one or more governmental entities comprises:

logging one or more corrections made to the one or more improper encounters.

15. The method of claim 11 further comprising:

determining, based on the one or more responses received from the one or more governmental entities, one or more rejected encounters of the one or more encounters that are rejected by the one or more governmental entities, wherein each of the one or more rejected encounters corresponds to one or more rejection statuses of the one or more responses;

correcting the one or more rejected encounters of the one or more encounters based on the one or more rejection statuses; and resubmitting the one or more rejected encounters, as corrected, to the one or more governmental entities.

16. The method of claim 15, wherein correcting the one or more rejected encounters of the one or more encounters based on the one or more rejection statuses comprises:

assigning the one or more rejected encounters to one or more response correction queues based on the one or more rejection statuses; and receiving one or more manual corrections for the one or more rejected encounters in the one or more response correction queues.

17. The method of claim 15, wherein correcting the one or more rejected encounters of the one or more encounters based on the one or more rejection statuses comprises:

logging one or more corrections made to the one or more rejected encounters.

18. The method of claim 11, wherein the one or more governmental entities comprise at least one of CMS or one or more State-based Medicaid entities.

19. The method of claim 11, wherein the one or more encounters are submitted to multiple different governmental entities.

20. The method of claim 11 further comprising:

integrating with each of the different user interface displays an XML editor configured to allow manual corrections to the one or more encounters.

* * * * *